United States Patent
Sheen et al.

(10) Patent No.: US 6,632,602 B1
(45) Date of Patent: Oct. 14, 2003

(54) PLANT SUGAR SENSORS AND USES THEREOF

(75) Inventors: Jen Sheen, Boston, MA (US); Jyan-Chyun Jang, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 08/622,191

(22) Filed: Mar. 25, 1996

(51) Int. Cl.$^7$ .................. C12N 15/00; C12Q 1/68; A01H 5/00
(52) U.S. Cl. .................. 435/6; 435/69.1; 435/410; 435/419; 435/320.1; 435/455; 536/23.1; 536/23.2; 536/23.6; 800/205
(58) Field of Search .................. 435/6, 69.1, 410, 435/419, 320.1, 455; 536/23.1, 23.2, 23.6; 800/205

(56) References Cited

FOREIGN PATENT DOCUMENTS

| EP | 0 438 904 A1 | 7/1991 |
|---|---|---|
| WO | WO 94/00563 | 1/1994 |

OTHER PUBLICATIONS

Boswell et al. "Sequence Comparison and Alignment: The Measurement and Interpretation of Sequence Similarity" in Computational Molecular Biology. Oxford University Press, pp. 161–168, 1988.*
Entian et al., "Cloning of Hexokinase Structural Genes from *Saccharomyces cerevisiae* Mutants with Regulatory Mutations Responsible for Glucose Repression," *Molecular and Cellular Biology* 5:3035–3040, 1985.
Entian et al., "Genetic and Biochemical Evidence for Hexokinase PII as a Key Enzyme Involved in Carbon Catabolite Repression in Yeast," *Molec. Gen. Genet.* 178:633–637, 1980.
Entian et al., "*Saccharomyces cerevisiae* Mutants Provide Evidence of Hexokinase PII as a Bifunctional Enzyme with Catalytic and Regulatory Domains for Triggering Carbon Catabolite Repression," *Journal of Bacteriology* 158:29–35, 1984.
Kriegel et al., "In Vivo Phosphorylation Site of Hexokinase 2 in *Saccharomyces cerevisiae*," *Biochemistry* 33:148–152, 1994.
Bork et al., "Convergent evolution of similar enzymatic function on different protein folds: The hexokinase, ribokinase, and galactokinase families of sugar kinases," *Protein Science* 2:31–40 (1993).
Halford et al., "Is hexokinase really a sugar sensor in plants?" *Trends Plant Sci.* 4:117–120 (1999).
Moore and Sheen, "Plant sugar sensing and signaling—a complex reality," *Trends Plant Sci.* 4:250 (1999).
Halford et al., "Reply . . . The sugar sensing story," *Trends Plant Sci.* 4:251 (1999).
Uhlmann and Peyman, "Antisense Oligonucleotides: A New Therapeutic Principle," *Chemical Reviews* 90:543–584 (1990).
Jyan–Chyun et al., The Plant Cell, 9:5–19 (1997).
Jang et al., Database GenBank on MPSRCH, Accession No. U28214 (Jun. 1995).
Dai et al., Database GenBank an MPSRCH, Accession No. U18754 (Jan. 1995).
Casper et al., *Plant Physiol.* 79, 11 (1985).
Chen et al., *Plant J.* 6, 625 (1994).
Dai et al., *Plant Physiol.* 108:879–880 (1995).
Dickinson et al., *Plant Physiol.* 95, 420 (1991).
Goldschmidt and Huber, *Plant Physiol.* 99, 1443 (1992).
Herbers et al., Plant Mol. Biol. 29, 1027 (1995).
Huber and Hanson, *Plant Physiol.* 99, 1449 (1992).
Jang and Sheen, *The Plant Cell* 6:1665–1679 (1994).
Knight and Gray, *Mol. Gen. Genet.* 242, 586 (1994).
Lam et al., *Plant Physiol.* 106, 1347 (1994).
Magnuson et al., *Proc. Natl. Acad. Sci. U.S.A.* 86, 4838 (1989).
Mita et al., *Plant Physiol.* 107, 895 (1995).
Nie et al., *Plant Physiol.* 108, 975 (1995).
Nishi et al., *Diabetologia* 35, 743 (1992).
Prior et al., *Mol. Cell. Biol.* 13, 3882 (1993).
Reynolds and Smith, *Plant Mol. Biol.* 29, 885 (1995).
Sheen, *The Plant Cell* 2:1027–1038 (1990).
Sheen, *Photosynthesis Research* 39:427–438 (1994).
Smith et al., *Plant Physiol.* 102, 1043 (1993).
Sonnewald et al., *Plant J.* 1, 95 (1991).
Sonnewald et al., Plant Responses to Sugar Accumulation in Transgenic Tobacco Plants, pp. 246–257, In: M. A. Madore, W. J. Lucas (eds.), *Carbon Partitioning and Source–Sink Interactions in Plants*, American Society of Plant Physiologists, Rockville, MD, (1995).
Stachelek et al., *Nucl. Acids Res.* 14, 945 (1986).
Stitt, *Plant Cell Environ.* 14, 741 (1991).
Stitt et al., *Planta* 183, 40 (1990).
Thomas and Rodriguez, *Plant Physiol.* 106, 1235 (1994).
Tsukaya et al., Plant Physiol. 97, 1414 (1991).
Van Oosten et al., *Plant Cell Environ.* 17, 913 (1994).
von Schaewen et al., *EMBO J.* 9, 3033 (1990).
*Arabidopsis thaliana* hexokinase, GenBank accession No. U18754.
*Arabidopsis thaliana* hexokinase, GenBank accession No. U28214.

* cited by examiner

*Primary Examiner*—Sean McGarry
(74) *Attorney, Agent, or Firm*—James D. DeCamp; Clark & Elbing, LLP

(57) ABSTRACT

Disclosed are methods and genes for manipulating the sugar-sensing capabilities of a plant, involving reducing or increasing the level of a hexokinase protein in a transgenic plant.

13 Claims, 14 Drawing Sheets

| | | | | | | |
|---|---|---|---|---|---|---|
| Athxk1 | . . . . . . . . . . | . . . . . . . . . . | . . . . . . . . . . | . . . . . MGKVAV | GATVVCTAAV | CAVAVLVVRR | RMQSSGKWGR | VLAILKAFEE | 46 |
| Athxk2 | . . . . . . . . . . | . . . . . . . . . . | . . . . . . . . . . | . . . . . MGKVAV | ATTVVCSVAV | CAAAALIVRR | RMKSAGKWAR | VIEILKAFEE | 46 |
| Human | . . . . . . . . . . | . . . . . . . . . . | . . . . . . . . . . | . . . . . . . . . . | . . . . . . . . . . | . . MLDDDR | ARMEAAKKEK | VE. . . .QILA | 21 |
| Rat | MAMDTTRCGA | QLLTLGTNKC | TNACSLLCRA | GTHNGHMNPR | CRTEQAAATQ | LPTCRVQLLL | 60 |
| Yeast1 | . . . . . . . . . . | . . . . . . . . . . | . . . . . . . . . . | . . . . . . . . . . | . . . . . . . .MV | HLGPKKPQAR | KGSMADVPKE | LMDEIHQLED | 32 |
| Yeast2 | . . . . . . . . . . | . . . . . . . . . . | . . . . . . . . . . | . . . . . . . . . . | . . . . . . . .MV | HLGPKKPQAR | KGSMADVPKE | LMQQIENFEK | 32 |
| Yeast3 | . . . . . . . . . . | . . . . . . . . . . | . . . . . . . . . . | . . . . . . . . . . | . . . . . . . .MV | RLGPKKPPAR | KGSMADVPAN | LMEQIHGLET | 32 |

| | | | | | | | | |
|---|---|---|---|---|---|---|---|---|
| Athxk1 | DCATPISKLR | QVADAMTVEM | HAG. .LASDG | GSKLKMLISY | VDNLPSGDEK | GLFYALDLGG | 104 |
| Athxk2 | DCATPIAKLR | QVADAMTVEM | HAG. .LASEG | GSKLKMLISY | VDNLPSGDET | GFFYALDLGG | 104 |
| Human | EFQLQEEDLK | KVMRRMQKEM | DRGLRLETHE | EASVKMLETV | VRSTPEGSEV | GDFLSLDLGG | 81 |
| Rat | NYHVEGRA. . | . . . .DPGRVP | AAGGRPEEGD | EPDAEGDGPW | PEAGDPRGEV | GDFLSLDLGG | 114 |
| Yeast1 | MFTVDSETLR | KVVKHFIDEL | NKG. . .LTKKG | V. .NIPMIPGW | YMEFPTGKES | GNVLAIDLGG | 89 |
| Yeast2 | IFTVPTETLQ | AVTKHFISEL | EKG. . .LSKKG | G. .NIPMIPGW | VMDFPTGKES | GDFLAIDLGG | 89 |
| Yeast3 | LFTVSSEKMR | SIVKHFISEL | DKG. . .LSKKG | G. .NIPMIPGW | VVEYPTGKET | GDFLALDLGG | 89 |

| | | | | | | | | |
|---|---|---|---|---|---|---|---|---|
| Athxk1 | TNFRVMRVLL | GGKQE. .RVV | KQEFEEVSIP | PHLMTGG. SD | ELENEIAEAL | AKFVATECED | 161 |
| Athxk2 | TNFRVMRVLL | GGKQE. .RVV | KREFKEESIP | PHLMTGK. SH | ELFDEIVDVL | AKFVATECED | 161 |
| Human | TNFRVMLVKV | GEGEEGQWSV | KTKHQMYSIP | EDAMTG. TAE | MLFDYISECI | SDFLDK. . . . . | 136 |
| Rat | TNFRVMLVKV | GEGEAGQWSV | KTKHQMYSIP | EDAMTG. TAE | MLFDYISECI | SDFLDK. . . . . | 169 |
| Yeast1 | TNLRVVLVKL | SGNRT. .FDT | TQS. . .KYKLP | HDMRTTKHQE | ELWSFIADSL | KDFMV. . .EQ | 142 |
| Yeast2 | TNLRVVLVKL | GGDRT. .FDT | TQS. . .KYRLP | DAMRTTQNPD | ELWEFIADSL | KAFID. . .EQ | 142 |
| Yeast3 | TNLRVLVKL | GGNHD. .FDT | TQN. . .KYRLP | DHLRTG. TSE | QLWSFIAKCL | KEEVD. . .EW | 141 |

```
Athxk1  MAEDAAFFGD TVPSKLRIPF IIRTPHMSAM HNDTSPDLKI VGSKIKDILE VPTTSLKMRK  393
Athxk2  MAEEAAFFGD IVPPKLKIPF IIRTPNMSAM HSDTSPDLKI VGSKLKDILE VQTSSLKMRK  393
Human   LVDENLLFHG EASEQLRTRG AFETRFVSQV ESDTGDRKQI YNILSTLGLR PSTT...DCD  365
Rat     LVDENLLFHG EASEQLRTRG AFETRFVSQV ESDSGDRKQI HNILSTLGLR PSVI...DCD  398
Yeast1  LNEKGLMLKD QDLSKLKQPY IMDTSYPARI EDDMFQKDFG VKTT.LPERK              379
Yeast2  MYKQGFIFKN QDLSKFDKPF VMDTSYPARI EDPFENLED  TDDLFQNEFG INTT.VQERK   379
Yeast3  LYDSGFIFKD QDISKLKEAY VMDTSYPSKI EDPFENLED  TDDLFKTNLN IETT.VVERK   378

Athxk1  VVISLCNIIA TRGARLSAAG IYGILKKLGR DTTKDEEVQK SVIAMDGGLF EHYTQFSECM   453
Athxk2  VVISLCNIIA SRGARLSAAG IYGILKKIGR DATKDGEAQK SVIAMDGGLF EHYTQFSESM   453
Human   IVRRACESVS TRAAHMCSAG LAGVINRM.. RESRSEDVMR ITVGVDGSVY KLHPSFKERF   423
Rat     IVRRACESVS TRAAHMCSAG LAGVINRM.. RESRSEDVMR ITVGVDGSVY KLHPSFKERF   456
Yeast1  LIRRLCELIG TRAARLAVCG IAAICQKRGY KTGH...... ..IAADGSVY NKYPGFKEAA   431
Yeast2  LIRRLSELIG ARAARLSVCG IAAICQKRGY KTGH...... ..IAADGSVY NRYPGFKEKA   431
Yeast3  LIRKLAELVG TRAARLTVCG VSAICDKRGY KTAH_..... ..IAADGSVF NRYPGYKEKA   430

Athxk1  ESSLKELLG. .DEASGSV   EVTHSNDGSG IGAALLAASH SLYLE...DS   .....496
Athxk2  KSSLKELLG. .DEVSESV   EVILSNDGSG VGAALLAASH SQYLELEDDS   ETS..502
Human   HASVRRL... .TPSCEI    TFIESEEGSG RGAALVSAVA CKKACMLGQ.  .....465
Rat     HASVRRL... .TPNCEI    TFIESEEGSG RGAALVSAVA CKKACMLAQ.  .....498
Yeast1  AKGLRDIYGW TGENASKDPI TIVPAEDGSG AGAAVIAALS EKRIAEGKVS   GIIGA486
Yeast2  ANALKDIYGW TQTSLDDYPI KIVPAEDGSG AGAAVIAALA QKRIAEGKSV   GIIGA486
Yeast3  AQALKDIYNW DVEKMEDHPI QLVAAEDGSG VGAAIIACLT QKRLAAGKSV   GIKGE485
```

Fig. 1B-3

```
   1 CAGTGTGAGT AATTTAGATC GGTATTAGAT CCATCTTAGG TTTCTCTAAT
  51 TTCTCTCAAT TCACTCCAAA ATTTTGATTA TTTCTTCTTT CTGGCTTGTC
 101 AATTTTAGTC ATTTGTAATC CTTGCTTTTG CGATCGGAAT CGTAAAAATC
 151 CGATCTTTCT TTTAGATTCG TTTTGTTTTT GATTCCAAAT CGGAAAAATG
 201 GGTAAAGTAG CTGTTGGAGC GACTGTTGTT TGCACGGCGG CGGTTTGTGC
 251 GGTGGCTGTT TTGGTTGTTC GACGACGGAT GCAGAGCTCA GGGAAGTGGG
 301 GACGTGTTTT GGCTATCCTC AAGGCCTTTG AAGAGGATTG TGCGACTCCG
 351 ATCTCGAAAC TGAGACAAGT GGCTGATGCT ATGACCGTTG AGATGCATGC
 401 TGGTCTTGCA TCCGACGGTG GTAGCAAACT CAAGATGCTT ATCAGCTACG
 451 TTGATAATCT TCCTTCCGGG GATGAAAAGG GTCTCTTTTA TGCATTGGAC
 501 CTAGGGGGGA CAAACTTCCG TGTCATGCGT GTGCTTCTTG GCGGGAAGCA
 551 AGAGCGTGTT GTTAAACAAG AATTCGAAGA AGTTTCGATT CCTCCTCATT
 601 TGATGACTGG TGGTTCAGAT GAGTTGTTCA ATTTTATAGC TGAAGCTCTT
 651 GCGAAGTTTG TCGCTACAGA ATGCGAAGAC TTTCATCTTC AGAAGGTAG
 701 ACAGAGGGAA TTAGGTTTCA CTTTCTCGTT TCCTGTTAAG CAGACTTCTC
 751 TGTCCTCTGG TAGTCTCATC AAATGGACAA AAGGCTTTTC CATCGAAGAA
 801 GCAGTTGGAC AAGATGTTGT TGGAGCACTT AATAAGGCTC TGGAAAGAGT
 851 TGGTCTTGAC ATGCGAATCG CAGCACTTGT TAATGATACC GTTGGAACAC
 901 TAGCCGGTGG TAGATACTAT AACCCGGATG TTGTTGCTGC TGTTATTTTA
 951 GGCACTGGGA CAAACGCAGC CTATGTTGAG CGTGCAACCG CGATCCCTAA
1001 ATGGCATGGT CTGCTTCCAA AATCAGGAGA AATGGTTATA AACATGGAAT
1051 GGGGAAACTT CAGGTCATCA CATCTTCCAT TAACCGAGTT TGATCACACG
1101 CTGGATTTCG AGAGTCTGAA TCCAGGCGAA CAGATTCTTG AGAAAATCAT
1151 TTCCGGTATG TACTTGGGAG AGATTTTGCG AAGAGTTCTT CTAAAGATGG
1201 CTGAAGATGC TGCTTTCTTT GGCGATACAG TCCCATCTAA GCTGAGAATA
1251 CCATTCATCA TTAGGACTCC TCACATGTCG GCTATGCACA ACGACACTTC
1301 TCCAGACTTG AAGATTGTTG GGAGCAAGAT TAAGGATATA TTGGAGGTCC
1351 CTACAACTTC TCTGAAAATG AGAAAGTTG  TGATCAGTCT CTGCAACATC
1401 ATAGCAACCC GAGGAGCTCG TCTCTCTGCT GCTGGAATCT ATGGTATTCT
1451 GAAGAAACTG GAAGAGATA CTACTAAAGA CGAGGAGGTG CAGAAATCGG
1501 TTATAGCCAT GGATGGTGGA TTGTTTGAGC ATTACACTCA GTTTAGTGAG
1551 TGTATGGAGA GCTCACTAAA AGAGTTGCTT GGAGATGAAG CTTCAGGAAG
1601 CGTTGAAGTC ACTCACTCCA ATGATGGATC AGGCATTGGA GCTGCGCTTC
1651 TTGCTGCTTC TCACTCTCTC TACCTTGAAG ACTCTTAAAA CCTACCCAAA
1701 GAGCGCCATT TTTCGGTAAT TTACTGAAAG CTTTTCGCTA TCAGAAAACG
1751 CCTAAGCCAA GTTCTAAGGC GTCATAAAAG AAAGCATTCC ATGTTTTTAC
1801 TCTTCCCCAA GACTTTCTTT GTAGCAAATA AGTTTCCTTG GGAGAAATAT
1851 TTGTTTTCAT GTTCTTCAAA AATAAAAGAC TCAGTTCTTC AGATTCTGGG
1901 ATTTTATTAT AACCAGATAT GTTGTAAAAA CTACAAATTC AAAGCTCACT
1951 TCACTGGAGT TCTGAGTATA TAAAGATTTC ATTTTTCCTA AAAAAAAAA
2001 AAAAACTAA  ATTACTCACA CTC
```

Fig. 1F

```
   1 CAGTGTGAGT AATTTAGATC ATCTCTAGCG TTCTTAAAGT TTCCAACTTT TTTTTTTTAT
  61 TAATTTGGGC CAACTTTTTT GTTTTATTAA TTTGGGCCAA CCTTTTTTGG TTTGAGAATT
 121 GGGCGAGGGA GAAAGATGGG TAAAGTGGCA GTTGCAACGA CGGTAGTGTG TTCGGTGGCG
 181 GTATGTGCGG CGGCGGCGTT GATAGTACGG AGGAGAATGA AAAGCGCAGG GAAATGGGCA
 241 AGAGTGATAG AGATATTGAA AGCCTTTGAA GAAGATTGTG CAACGCCAAT TGCCAAATTG
 301 AGACAAGTGG CTGATGCTAT GACTGTTGAG ATGCATGCTG GTCTTGCTTC TGAAGGTGGC
 361 AGCAAGCTTA AGATGCTTAT TAGCTACGTT GATAATCTTC CTTCTGGGGA TGAGACTGGT
 421 TTTTTCTATG CGTTGGATCT AGGCGGAACA AACTTCCGTG TTATGCGTGT GCTTCTTGGT
 481 GGGAAGCACG ACCGTGTTGT TAAACGAGAA TTCAAAGAAG AATCTATTCC TCCTCATTTG
 541 ATGACCGGGA AGTCACATGA ATTATTCGAT TTTATCGTTG ATGTTCTTGC CAAGTTTGTC
 601 GCTACAGAAG GCGAGGACTT TCATCTCCCA CCTGGTAGAC AACGGGAACT AGGTTTCACT
 661 TTCTCATTTC CGGTTAAGCA GCTATCTTTA TCCTCTGGCA CTCTCATCAA CTGGACAAAG
 721 GGCTTTTCCA TTGACGATAC AGTTGATAAA GATGTTGTTG AGAACTTGT TAAAGCTATG
 781 GAAAGAGTTG GCTGGACAT GCTTGTCGCA GCGCTTGTTA ATGATACCAT TGGAACACTT
 841 GCGGGTGGTA GATACACTAA CCCGGATGTC GTTGTCGCAG TTATTTTGGG CACCGGCACA
 901 AATGCAGCCT ATGTCGAACG TGCACATGCA ATTCCCAAAT GGCATGGTTT GCTACCCAAA
 961 TCAGGAGAAA TGGTGATCAA CATGGAATGG GGAAACTTCA GGTCATCACA TCTTCCATTG
1021 ACAGAGTACG ACCACTCTCT AGATGTCGAT AGTTTGAATC CTGGTGAACA GATTCTTGAG
1081 AAAATCATTT CCGGAATGTA TCTGGGAGAA ATCTTGCGTA GAGTTCTTCT GAAGATGGCT
1141 GAAGAAGCTG CCTTCTTTGG CGATATCGTC CCACCTAAGC TGAAAATACC ATTCATCATA
1201 AGGACCCCCA ACATGTCTGC TATGCACAGT GATACTTCCC CGGATTTGAA GGTTGTAGGA
1261 AGCAAGTTAA AAGACATATT GGAGGTCCAG ACTAGTTCTC TGAAGATGAG GAAAGTTGTG
1321 ATCAGCCTAT GTAACATCAT TGCAAGCCGA GGAGCTCGTT TATCTGCTGC GGGGATCTAT
1381 GGAATCCTCA AGAAAATAGG AAGAGACGCA ACAAAAGATG GAGAAGCTCA GAAATCTGTG
1441 ATAGCGATGG ACGGTGGGCT ATTCGAGCAT ACACTCAGT TCAGTGAGTC GATGAAGAGT
1501 TCATTGAAAG AGTTGCTTGG AGATGAAGTT TCAGAGAGTG TTGAAGTGAT ACTGTCGAAT
1561 GATGGTTCAG GTGTTGGAGC TGCATTACTT GCTGCTTCTC ACTCTCAGTA TCTCGAACTT
1621 GAAGATGACT CTGAAACAAG TTAATTTAAA GCTTTTTTGT GTTTAACCTT CTTCTTGTTG
1681 CGTAGGTTAA CAATAAAAGT AGAGGTAAAT GCCTTTGGGA AATTTTATTT TTGACAATTT
1741 TCAGGAACAA TAAAACCTGG ATTCTTCATC AAAGCTCTGG GAAATTCAAA CGACCAGCCA
1801 ATGTTGTAGA ACTATACATA TATATTCGAG TTCTTTCTAT GAAAAAAAAA AAAAAAAAA
1861 AACCTTAAAT TACTCACACT GGC
```

Fig. 1G

SEQUENCE LISTING

<160> NUMBER OF SEQ ID NOS: 13

<210> SEQ ID NO 1
<211> LENGTH: 496
<212> TYPE: PRT
<213> ORGANISM: Arabidopsis thaliana

<400> SEQUENCE: 1

```
Met Gly Lys Val Ala Val Gly Ala Thr Val Val Cys Thr Ala Ala Val
1               5                   10                  15

Cys Ala Val Ala Val Leu Val Val Arg Arg Arg Met Gln Ser Ser Gly
            20                  25                  30

Lys Trp Gly Arg Val Leu Ala Ile Leu Lys Ala Phe Glu Glu Asp Cys
        35                  40                  45

Ala Thr Pro Ile Ser Lys Leu Arg Gln Val Ala Asp Ala Met Thr Val
    50                  55                  60

Glu Met His Ala Gly Leu Ala Ser Asp Gly Gly Ser Lys Leu Lys Met
65                  70                  75                  80

Leu Ile Ser Tyr Val Asp Asn Leu Pro Ser Gly Asp Glu Lys Gly Leu
                85                  90                  95

Phe Tyr Ala Leu Asp Leu Gly Gly Thr Asn Phe Arg Val Met Arg Val
            100                 105                 110

Leu Leu Gly Gly Lys Gln Glu Arg Val Val Lys Gln Glu Phe Glu Glu
        115                 120                 125

Val Ser Ile Pro Pro His Leu Met Thr Gly Gly Ser Asp Glu Leu Phe
    130                 135                 140

Asn Phe Ile Ala Glu Ala Leu Ala Lys Phe Val Ala Thr Glu Cys Glu
145                 150                 155                 160
```

-continued

```
Asp Phe His Leu Pro Glu Gly Arg Gln Arg Glu Leu Gly Phe Thr Phe
            165                 170                 175
Ser Phe Pro Val Lys Gln Thr Ser Leu Ser Ser Gly Ser Leu Ile Lys
            180                 185                 190
Trp Thr Lys Gly Phe Ser Ile Glu Glu Ala Val Gly Gln Asp Val Val
            195                 200                 205
Gly Ala Leu Asn Lys Ala Leu Glu Arg Val Gly Leu Asp Met Arg Ile
            210                 215                 220
Ala Ala Leu Val Asn Asp Thr Val Gly Thr Leu Ala Gly Gly Arg Tyr
225                 230                 235                 240
Tyr Asn Pro Asp Val Val Ala Ala Val Ile Leu Gly Thr Gly Thr Asn
                    245                 250                 255
Ala Ala Tyr Val Glu Arg Ala Thr Ala Ile Pro Lys Trp His Gly Leu
                    260                 265                 270
Leu Pro Lys Ser Gly Glu Met Val Ile Asn Met Glu Trp Gly Asn Phe
            275                 280                 285
Arg Ser Ser His Leu Pro Leu Thr Glu Phe Asp His Thr Leu Asp Phe
            290                 295                 300
Glu Ser Leu Asn Pro Gly Glu Gln Ile Leu Glu Lys Ile Ile Ser Gly
305                 310                 315                 320
Met Tyr Leu Gly Glu Ile Leu Arg Arg Val Leu Leu Lys Met Ala Glu
                    325                 330                 335
Asp Ala Ala Phe Phe Gly Asp Thr Val Pro Ser Lys Leu Arg Ile Pro
                    340                 345                 350
Phe Ile Ile Arg Thr Pro His Met Ser Ala Met His Asn Asp Thr Ser
            355                 360                 365
Pro Asp Leu Lys Ile Val Gly Ser Lys Ile Lys Asp Ile Leu Glu Val
            370                 375                 380
Pro Thr Thr Ser Leu Lys Met Arg Lys Val Val Ile Ser Leu Cys Asn
385                 390                 395                 400
Ile Ile Ala Thr Arg Gly Ala Arg Leu Ser Ala Ala Gly Ile Tyr Gly
                    405                 410                 415
Ile Leu Lys Lys Leu Gly Arg Asp Thr Thr Lys Asp Glu Glu Val Gln
                    420                 425                 430
Lys Ser Val Ile Ala Met Asp Gly Gly Leu Phe Glu His Tyr Thr Gln
            435                 440                 445
Phe Ser Glu Cys Met Glu Ser Ser Leu Lys Glu Leu Leu Gly Asp Glu
            450                 455                 460
Ala Ser Gly Ser Val Glu Val Thr His Ser Asn Asp Gly Ser Gly Ile
465                 470                 475                 480
Gly Ala Ala Leu Leu Ala Ala Ser His Ser Leu Tyr Leu Glu Asp Ser
                    485                 490                 495

<210> SEQ ID NO 2
<211> LENGTH: 502
<212> TYPE: PRT
<213> ORGANISM: Arabidopsis thaliana

<400> SEQUENCE: 2

Met Gly Lys Val Ala Val Ala Thr Thr Val Val Cys Ser Val Ala Val
  1               5                  10                  15
Cys Ala Ala Ala Ala Leu Ile Val Arg Arg Arg Met Lys Ser Ala Gly
                 20                  25                  30
Lys Trp Ala Arg Val Ile Glu Ile Leu Lys Ala Phe Glu Glu Asp Cys
```

```
                35                  40                  45
Ala Thr Pro Ile Ala Lys Leu Arg Gln Val Ala Asp Ala Met Thr Val
        50                  55                  60
Glu Met His Ala Gly Leu Ala Ser Glu Gly Ser Lys Leu Lys Met
65                  70                  75                  80
Leu Ile Ser Tyr Val Asp Asn Leu Pro Ser Gly Asp Glu Thr Gly Phe
                85                  90                  95
Phe Tyr Ala Leu Asp Leu Gly Gly Thr Asn Phe Arg Val Met Arg Val
                100                 105                 110
Leu Leu Gly Gly Lys His Asp Arg Val Val Lys Arg Glu Phe Lys Glu
                115                 120                 125
Glu Ser Ile Pro Pro His Leu Met Thr Gly Lys Ser His Glu Leu Phe
            130                 135                 140
Asp Phe Ile Val Asp Val Leu Ala Lys Phe Val Ala Thr Glu Gly Glu
145                 150                 155                 160
Asp Phe His Leu Pro Pro Gly Arg Gln Arg Glu Leu Gly Phe Thr Phe
                165                 170                 175
Ser Phe Pro Val Lys Gln Leu Ser Leu Ser Ser Gly Thr Leu Ile Asn
            180                 185                 190
Trp Thr Lys Gly Phe Ser Ile Asp Asp Thr Val Asp Lys Asp Val Val
            195                 200                 205
Gly Glu Leu Val Lys Ala Met Glu Arg Val Gly Leu Asp Met Leu Val
        210                 215                 220
Ala Ala Leu Val Asn Asp Thr Ile Gly Thr Leu Ala Gly Gly Arg Tyr
225                 230                 235                 240
Thr Asn Pro Asp Val Val Ala Val Ile Leu Gly Thr Gly Thr Asn
                245                 250                 255
Ala Ala Tyr Val Glu Arg Ala His Ala Ile Pro Lys Trp His Gly Leu
            260                 265                 270
Leu Pro Lys Ser Gly Glu Met Val Ile Asn Met Glu Trp Gly Asn Phe
        275                 280                 285
Arg Ser Ser His Leu Pro Leu Thr Glu Tyr Asp His Ser Leu Asp Val
        290                 295                 300
Asp Ser Leu Asn Pro Gly Glu Gln Ile Leu Glu Lys Ile Ile Ser Gly
305                 310                 315                 320
Met Tyr Leu Gly Glu Ile Leu Arg Arg Val Leu Leu Lys Met Ala Glu
                325                 330                 335
Glu Ala Ala Phe Phe Gly Asp Ile Val Pro Pro Lys Leu Lys Ile Pro
                340                 345                 350
Phe Ile Ile Arg Thr Pro Asn Met Ser Ala Met His Ser Asp Thr Ser
            355                 360                 365
Pro Asp Leu Lys Val Val Gly Ser Lys Leu Lys Asp Ile Leu Glu Val
        370                 375                 380
Gln Thr Ser Ser Leu Lys Met Arg Lys Val Val Ile Ser Leu Cys Asn
385                 390                 395                 400
Ile Ile Ala Ser Arg Gly Ala Arg Leu Ser Ala Ala Gly Ile Tyr Gly
                405                 410                 415
Ile Leu Lys Lys Ile Gly Arg Asp Ala Thr Lys Asp Gly Glu Ala Gln
            420                 425                 430
Lys Ser Val Ile Ala Met Asp Gly Gly Leu Phe Glu His Tyr Thr Gln
            435                 440                 445
Phe Ser Glu Ser Met Lys Ser Ser Leu Lys Glu Leu Leu Gly Asp Glu
450                 455                 460
```

```
Val Ser Glu Ser Val Glu Val Ile Leu Ser Asn Asp Gly Ser Gly Val
465                 470                 475                 480

Gly Ala Ala Leu Leu Ala Ala Ser His Ser Gln Tyr Leu Glu Leu Glu
                485                 490                 495

Asp Asp Ser Glu Thr Ser
            500

<210> SEQ ID NO 3
<211> LENGTH: 2023
<212> TYPE: DNA
<213> ORGANISM: Arabidopsis thaliana
<220> FEATURE:
<221> NAME/KEY: CDS
<222> LOCATION: (198)...(2023)

<400> SEQUENCE: 3
cagtgtgagt aatttagatc ggtattagat ccatcttagg tttctctaat ttctctcaat      60
tcactccaaa attttgatta tttcttcttt ctggcttgtc aattttagtc atttgtaatc     120
cttgcttttg cgatcggaat cgtaaaaatc cgatctttct tttagattcg ttttgttttt     180
gattccaaat cggaaaa atg ggt aaa gta gct gtt gga gcg act gtt gtt        230
                   Met Gly Lys Val Ala Val Gly Ala Thr Val Val
                    1               5                  10 tgc acg gcg gcg gtt tgt gcg gtg gct gtt ttg gtt gtt cga cga cgg       278
Cys Thr Ala Ala Val Cys Ala Val Ala Val Leu Val Val Arg Arg Arg
            15                  20                  25 atg cag agc tca ggg aag tgg gga cgt gtt ttg gct atc ctc aag gcc       326
Met Gln Ser Ser Gly Lys Trp Gly Arg Val Leu Ala Ile Leu Lys Ala
        30                  35                  40 ttt gaa gag gat tgt gcg act ccg atc tcg aaa ctg aga caa gtg gct       374
Phe Glu Glu Asp Cys Ala Thr Pro Ile Ser Lys Leu Arg Gln Val Ala
    45                  50                  55 gat gct atg acc gtt gag atg cat gct ggt ctt gca tcc gac ggt ggt       422
Asp Ala Met Thr Val Glu Met His Ala Gly Leu Ala Ser Asp Gly Gly
60                  65                  70                  75 agc aaa ctc aag atg ctt atc agc tac gtt gat aat ctt cct tcc ggg       470
Ser Lys Leu Lys Met Leu Ile Ser Tyr Val Asp Asn Leu Pro Ser Gly
                80                  85                  90 gat gaa aag ggt ctc ttt tat gca ttg gac cta ggg ggg aca aac ttc       518
Asp Glu Lys Gly Leu Phe Tyr Ala Leu Asp Leu Gly Gly Thr Asn Phe
            95                 100                 105 cgt gtc atg cgt gtg ctt ctt ggc ggg aag caa gag cgt gtt gtt aaa       566
Arg Val Met Arg Val Leu Leu Gly Gly Lys Gln Glu Arg Val Val Lys
        110                 115                 120 caa gaa ttc gaa gaa gtt tcg att cct cct cat ttg atg act ggt ggt       614
Gln Glu Phe Glu Glu Val Ser Ile Pro Pro His Leu Met Thr Gly Gly
    125                 130                 135 tca gat gag ttg ttc aat ttt ata gct gaa gct ctt gcg aag ttt gtc       662
Ser Asp Glu Leu Phe Asn Phe Ile Ala Glu Ala Leu Ala Lys Phe Val
140                 145                 150                 155 gct aca gaa tgc gaa gac ttt cat ctt cca gaa ggt aga cag agg gaa       710
Ala Thr Glu Cys Glu Asp Phe His Leu Pro Glu Gly Arg Gln Arg Glu
                160                 165                 170 tta ggt ttc act ttc tcg ttt cct gtt aag cag act tct ctg tcc tct       758
Leu Gly Phe Thr Phe Ser Phe Pro Val Lys Gln Thr Ser Leu Ser Ser
            175                 180                 185 ggt agt ctc atc aaa tgg aca aaa ggc ttt tcc atc gaa gaa gca gtt       806
Gly Ser Leu Ile Lys Trp Thr Lys Gly Phe Ser Ile Glu Glu Ala Val
        190                 195                 200
```

-continued

| | | |
|---|---|---|
| gga caa gat gtt gtt gga gca ctt aat aag gct ctg gaa aga gtt ggt<br>Gly Gln Asp Val Val Gly Ala Leu Asn Lys Ala Leu Glu Arg Val Gly<br>205                    210                    215 | 854 |
| ctt gac atg cga atc gca gca ctt gtt aat gat acc gtt gga aca cta<br>Leu Asp Met Arg Ile Ala Ala Leu Val Asn Asp Thr Val Gly Thr Leu<br>220                    225                    230                    235 | 902 |
| gcc ggt ggt aga tac tat aac ccg gat gtt gtt gct gct gtt att tta<br>Ala Gly Gly Arg Tyr Tyr Asn Pro Asp Val Val Ala Ala Val Ile Leu<br>                    240                    245                    250 | 950 |
| ggc act ggg aca aac gca gcc tat gtt gag cgt gca acc gcg atc cct<br>Gly Thr Gly Thr Asn Ala Ala Tyr Val Glu Arg Ala Thr Ala Ile Pro<br>                255                    260                    265 | 998 |
| aaa tgg cat ggt ctg ctt cca aaa tca gga gaa atg gtt ata aac atg<br>Lys Trp His Gly Leu Leu Pro Lys Ser Gly Glu Met Val Ile Asn Met<br>      270                    275                    280 | 1046 |
| gaa tgg gga aac ttc agg tca tca cat ctt cca tta acc gag ttt gat<br>Glu Trp Gly Asn Phe Arg Ser Ser His Leu Pro Leu Thr Glu Phe Asp<br>285                    290                    295 | 1094 |
| cac acg ctg gat ttc gag agt ctg aat cca ggc gaa cag att ctt gag<br>His Thr Leu Asp Phe Glu Ser Leu Asn Pro Gly Glu Gln Ile Leu Glu<br>300                    305                    310                    315 | 1142 |
| aaa atc att tcc ggt atg tac ttg gga gag att ttg cga aga gtt ctt<br>Lys Ile Ile Ser Gly Met Tyr Leu Gly Glu Ile Leu Arg Arg Val Leu<br>                    320                    325                    330 | 1190 |
| cta aag atg gct gaa gat gct gct ttc ttt ggc gat aca gtc cca tct<br>Leu Lys Met Ala Glu Asp Ala Ala Phe Phe Gly Asp Thr Val Pro Ser<br>              335                    340                    345 | 1238 |
| aag ctg aga ata cca ttc atc att agg act cct cac atg tcg gct atg<br>Lys Leu Arg Ile Pro Phe Ile Ile Arg Thr Pro His Met Ser Ala Met<br>          350                    355                    360 | 1286 |
| cac aac gac act tct cca gac ttg aag att gtt ggg agc aag att aag<br>His Asn Asp Thr Ser Pro Asp Leu Lys Ile Val Gly Ser Lys Ile Lys<br>365                    370                    375 | 1334 |
| gat ata ttg gag gtc cct aca act tct ctg aaa atg aga aaa gtt gtg<br>Asp Ile Leu Glu Val Pro Thr Thr Ser Leu Lys Met Arg Lys Val Val<br>380                    385                    390                    395 | 1382 |
| atc agt ctc tgc aac atc ata gca acc cga gga gct cgt ctc tct gct<br>Ile Ser Leu Cys Asn Ile Ile Ala Thr Arg Gly Ala Arg Leu Ser Ala<br>                400                    405                    410 | 1430 |
| gct gga atc tat ggt att ctg aag aaa ctg gga aga gat act act aaa<br>Ala Gly Ile Tyr Gly Ile Leu Lys Lys Leu Gly Arg Asp Thr Thr Lys<br>              415                    420                    425 | 1478 |
| gac gag gag gtg cag aaa tcg gtt ata gcc atg gat ggt gga ttg ttt<br>Asp Glu Glu Val Gln Lys Ser Val Ile Ala Met Asp Gly Gly Leu Phe<br>          430                    435                    440 | 1526 |
| gag cat tac act cag ttt agt gag tgt atg gag agc tca cta aaa gag<br>Glu His Tyr Thr Gln Phe Ser Glu Cys Met Glu Ser Ser Leu Lys Glu<br>445                    450                    455 | 1574 |
| ttg ctt gga gat gaa gct tca gga agc gtt gaa gtc act cac tcc aat<br>Leu Leu Gly Asp Glu Ala Ser Gly Ser Val Glu Val Thr His Ser Asn<br>460                    465                    470                    475 | 1622 |
| gat gga tca ggc att gga gct gcg ctt ctt gct gct tct cac tct ctc<br>Asp Gly Ser Gly Ile Gly Ala Ala Leu Leu Ala Ala Ser His Ser Leu<br>                480                    485                    490 | 1670 |
| tac ctt gaa gac tct taa aac cta ccc aaa gag cgc att ttt tcg gta<br>Tyr Leu Glu Asp Ser     Asn Leu Pro Lys Glu Arg His Phe Ser Val<br>              495                          500                    505 | 1718 |
| att tac tga aag ctt ttc gct atc aga aaa cgc cta agc caa gtt cta<br>Ile Tyr     Lys Leu Phe Ala Ile Arg Lys Arg Leu Ser Gln Val Leu<br>          510                    515                    520 | 1766 |

|  |  |  |  |  |  |  |  |  |  |  |  |  |
|---|---|---|---|---|---|---|---|---|---|---|---|---|
| agg | cgt | cat | aaa | aga | aag | cat | tcc | atg | ttt | tta | ctc | ttc | ccc | aag | act | 1814 |
| Arg | Arg | His | Lys | Arg | Lys | His | Ser | Met | Phe | Leu | Leu | Phe | Pro | Lys | Thr |  |
|  | 525 |  |  |  |  | 530 |  |  |  |  | 535 |  |  |  |  |  |

| ttc | ttt | gta | gca | aat | aag | ttt | cct | tgg | gag | aaa | tat | ttg | ttt | tca | tgt | 1862 |
|---|---|---|---|---|---|---|---|---|---|---|---|---|---|---|---|---|
| Phe | Phe | Val | Ala | Asn | Lys | Phe | Pro | Trp | Glu | Lys | Tyr | Leu | Phe | Ser | Cys |  |
| 540 |  |  |  |  | 545 |  |  |  |  | 550 |  |  |  |  | 555 |  |

| tct | tca | aaa | ata | aaa | gac | tca | gtt | ctt | cag | att | ctg | gga | ttt | tat | tat | 1910 |
|---|---|---|---|---|---|---|---|---|---|---|---|---|---|---|---|---|
| Ser | Ser | Lys | Ile | Lys | Asp | Ser | Val | Leu | Gln | Ile | Leu | Gly | Phe | Tyr | Tyr |  |
|  |  |  |  | 560 |  |  |  |  | 565 |  |  |  |  | 570 |  |  |

| aac | cag | ata | tgt | tgt | aaa | aac | tac | aaa | ttc | aaa | gct | cac | ttc | act | gga | 1958 |
|---|---|---|---|---|---|---|---|---|---|---|---|---|---|---|---|---|
| Asn | Gln | Ile | Cys | Cys | Lys | Asn | Tyr | Lys | Phe | Lys | Ala | His | Phe | Thr | Gly |  |
|  |  |  | 575 |  |  |  |  | 580 |  |  |  |  | 585 |  |  |  |

| gtt | ctg | agt | ata | taa | aga | ttt | cat | ttt | tcc | taa | aaa | aaa | aaa | aaa | aaa | 2006 |
|---|---|---|---|---|---|---|---|---|---|---|---|---|---|---|---|---|
| Val | Leu | Ser | Ile |  | Arg | Phe | His | Phe | Ser |  | Lys | Lys | Lys | Lys | Lys |  |
|  | 590 |  |  |  |  |  | 595 |  |  |  |  | 600 |  |  |  |  |

| cta | aat | tac | tca | cac | tc |  | 2023 |
|---|---|---|---|---|---|---|---|
| Leu | Asn | Tyr | Ser | His |  |  |  |
|  | 605 |  |  |  |  |  |  |

<210> SEQ ID NO 4
<211> LENGTH: 1883
<212> TYPE: DNA
<213> ORGANISM: Arabidopsis thaliana

<400> SEQUENCE: 4

| | |
|---|---|
| cagtgtgagt aatttagatc atctctagcg ttcttaaagt ttccaacttt ttttttttat | 60 |
| taatttgggc caactttttt gttttattaa tttgggccaa ccttttttgg tttgagaatt | 120 |
| gggcgaggga gaaagatggg taaagtggca gttgcaacga cggtagtgtg ttcggtggcg | 180 |
| gtatgtgcgg cggcggcgtt gatagtacgg aggagaatga aaagcgcagg gaaatgggca | 240 |
| agagtgatag agatattgaa agcctttgaa gaagattgtg caacgccaat tgccaaattg | 300 |
| agacaagtgg ctgatgctat gactgttgag atgcatgctg gtcttgcttc tgaaggtggc | 360 |
| agcaagctta gatgcttat tagctacgtt gataatcttc cttctgggga tgagactggt | 420 |
| tttttctatg cgttggatct aggcggaaca aacttccgtg ttatgcgtgt gcttcttggt | 480 |
| gggaagcacg accgtgttgt taaacgaaa ttcaaagaag aatctattcc tcctcatttg | 540 |
| atgaccggga agtcacatga attattcgat tttatcgttg atgttcttgc caagtttgtc | 600 |
| gctacagaag gcgaggactt tcatctccca cctggtagac aacgggaact aggtttcact | 660 |
| ttctcatttc cggttaagca gctatctta tcctctggca ctctcatcaa ctggacaaag | 720 |
| ggcttttcca ttgacgatac agttgataaa gatgttgttg gagaacttgt taaagctatg | 780 |
| gaaagagttg ggctggacat gcttgtcgca gcgcttgtta atgataccat ggaacactt | 840 |
| gcgggtggta gatacactaa cccggatgtc gttgtcgcag ttattttggg caccggcaca | 900 |
| aatgcagcct atgtcgaacg tgcacatgca attcccaaat ggcatggttt gctacccaaa | 960 |
| tcaggagaaa tggtgatcaa catggaatgg ggaaacttca ggtcatcaca tcttccattg | 1020 |
| acagagtacg accactctct agatgtcgat agtttgaatc ctggtgaaca gattcttgag | 1080 |
| aaaatcattt ccggaatgta tctgggagaa atcttgcgta gagttcttct gaagatggct | 1140 |
| gaagaagctg ccttctttgg cgatatcgtc ccacctaagc tgaaaatacc attcatcata | 1200 |
| aggaccccca acatgtctgc tatgcacagt gatacttccc cggatttgaa ggttgtagga | 1260 |
| agcaagttaa aagacatatt ggaggtccag actagttctc tgaagatgag gaaagttgtg | 1320 |
| atcagcctat gtaacatcat tgcaagccga ggagctcgtt tatctgctgc ggggatctat | 1380 |

-continued

```
ggaatcctca agaaaatagg aagagacgca acaaaagatg gagaagctca gaaatctgtg    1440
atagcgatgg acgtgggct attcgagcat acactcagt tcagtgagtc gatgaagagt      1500
tcattgaaag agttgcttgg agatgaagtt tcagagagtg ttgaagtgat actgtcgaat    1560
gatggttcag gtgttggagc tgcattactt gctgcttctc actctcagta tctcgaactt    1620
gaagatgact ctgaaacaag ttaatttaaa gctttttgt gtttaacctt cttcttgttg     1680
cgtaggttaa caataaaagt agaggtaaat gcctttggga aattttattt ttgacaattt    1740
tcaggaacaa taaaacctgg attcttcatc aaagctctgg gaaattcaaa cgaccagcca    1800
atgttgtaga actatacata tatattcgag ttctttctat gaaaaaaaaa aaaaaaaaaa    1860
aaccttaaat tactcacact ggc                                            1883
```

<210> SEQ ID NO 5
<211> LENGTH: 465
<212> TYPE: PRT
<213> ORGANISM: Homo sapiens

<400> SEQUENCE: 5

```
Met Leu Asp Asp Arg Ala Arg Met Glu Ala Ala Lys Lys Glu Lys Val
 1               5                  10                  15

Glu Gln Ile Leu Ala Glu Phe Gln Leu Gln Glu Glu Asp Leu Lys Lys
            20                  25                  30

Val Met Arg Arg Met Gln Lys Glu Met Asp Arg Gly Leu Arg Leu Glu
        35                  40                  45

Thr His Glu Glu Ala Ser Val Lys Met Leu Pro Thr Tyr Val Arg Ser
    50                  55                  60

Thr Pro Glu Gly Ser Glu Val Gly Asp Phe Leu Ser Leu Asp Leu Gly
65                  70                  75                  80

Gly Thr Asn Phe Arg Val Met Leu Val Lys Val Gly Glu Gly Glu Glu
                85                  90                  95

Gly Gln Trp Ser Val Lys Thr Lys His Gln Met Tyr Ser Ile Pro Glu
            100                 105                 110

Asp Ala Met Thr Gly Thr Ala Glu Met Leu Phe Asp Tyr Ile Ser Glu
        115                 120                 125

Cys Ile Ser Asp Phe Leu Asp Lys His Gln Met Lys His Lys Lys Leu
    130                 135                 140

Pro Leu Gly Phe Thr Phe Ser Phe Pro Val Arg His Glu Asp Ile Asp
145                 150                 155                 160

Lys Gly Ile Leu Leu Asn Gln Thr Lys Gly Phe Lys Ala Ser Gly Ala
                165                 170                 175

Glu Gly Asn Asn Val Val Gly Leu Leu Arg Asp Ala Ile Lys Arg Arg
            180                 185                 190

Gly Asp Phe Glu Met Asp Val Val Ala Met Val Asn Asp Thr Val Ala
        195                 200                 205

Thr Met Ile Ser Cys Tyr Tyr Glu Asp His Gln Cys Glu Val Gly Met
    210                 215                 220

Ile Val Gly Thr Gly Cys Asn Ala Cys Tyr Met Glu Glu Met Gln Asn
225                 230                 235                 240

Val Glu Leu Val Glu Gly Asp Glu Gly Arg Met Cys Val Asn Thr Glu
                245                 250                 255

Gln Gly Ala Phe Gly Asp Ser Gly Glu Leu Asp Glu Phe Leu Leu Glu
            260                 265                 270

Tyr Asp Arg Met Val Asp Glu Ser Ser Ala Asn Pro Gly Gln Gln Leu
        275                 280                 285
```

-continued

```
Tyr Glu Lys Leu Ile Gly Gly Lys Thr Met Gly Glu Leu Val Arg Leu
    290                 295                 300

Val Leu Leu Arg Leu Val Asp Glu Asn Leu Leu Phe His Gly Glu Ala
305                 310                 315                 320

Ser Glu Gln Leu Arg Thr Arg Gly Ala Phe Glu Thr Arg Phe Val Ser
                325                 330                 335

Gln Val Glu Ser Asp Thr Gly Asp Arg Lys Gln Ile Tyr Asn Ile Leu
            340                 345                 350

Ser Thr Leu Gly Leu Arg Pro Ser Thr Thr Asp Cys Asp Ile Val Arg
        355                 360                 365

Arg Ala Cys Glu Ser Val Ser Thr Arg Ala Ala His Met Cys Ser Ala
    370                 375                 380

Gly Leu Ala Gly Val Ile Asn Arg Met Arg Glu Ser Arg Ser Glu Asp
385                 390                 395                 400

Val Met Arg Ile Thr Val Gly Val Asp Gly Ser Val Tyr Lys Leu His
                405                 410                 415

Pro Ser Phe Lys Glu Arg Phe His Ala Ser Val Arg Arg Leu Thr Pro
            420                 425                 430

Ser Cys Glu Ile Thr Phe Ile Glu Ser Glu Glu Gly Ser Gly Arg Gly
        435                 440                 445

Ala Ala Leu Val Ser Ala Val Ala Cys Lys Lys Ala Cys Met Leu Gly
    450                 455                 460

Gln
465

<210> SEQ ID NO 6
<211> LENGTH: 498
<212> TYPE: PRT
<213> ORGANISM: Rattus norvegicus

<400> SEQUENCE: 6

Met Ala Met Asp Thr Thr Arg Cys Gly Ala Gln Leu Leu Thr Leu Gly
1               5                   10                  15

Thr Asn Lys Cys Thr Asn Ala Cys Ser Leu Leu Cys Arg Ala Gly Thr
            20                  25                  30

His Asn Gly His Met Asn Pro Arg Cys Arg Thr Glu Gln Ala Ala Ala
        35                  40                  45

Thr Gln Leu Pro Thr Cys Arg Val Gln Leu Leu Met Tyr His Val
    50                  55                  60

Glu Gly Arg Ala Asp Pro Gly Arg Val Pro Ala Ala Gly Gly Arg Pro
65                  70                  75                  80

Glu Glu Gly Asp Glu Pro Asp Ala Glu Gly Asp Gly Pro Trp Pro Glu
                85                  90                  95

Ala Gly Asp Pro Arg Gly Glu Val Gly Asp Phe Leu Ser Leu Asp Leu
            100                 105                 110

Gly Gly Thr Asn Phe Arg Val Met Leu Val Lys Val Gly Glu Gly Glu
        115                 120                 125

Ala Gly Gln Trp Ser Val Lys Thr Lys His Gln Met Tyr Ser Ile Pro
    130                 135                 140

Glu Asp Ala Met Thr Gly Thr Ala Glu Met Leu Phe Asp Tyr Ile Ser
145                 150                 155                 160

Glu Cys Ile Ser Asp Phe Leu Asp Lys His Gln Met Lys His Lys Lys
                165                 170                 175

Leu Pro Leu Gly Phe Thr Phe Ser Phe Pro Val Arg His Glu Asp Leu
```

-continued

```
                180                 185                 190
Asp Lys Gly Ile Leu Asn Trp Thr Lys Gly Phe Lys Ala Ser Gly
            195                 200                 205
Ala Glu Gly Asn Asn Ile Val Gly Leu Leu Arg Asp Ala Ile Lys Arg
            210                 215                 220
Arg Gly Asp Phe Glu Met Asp Val Val Ala Met Val Asn Asp Thr Val
225                 230                 235                 240
Ala Thr Met Ile Ser Cys Tyr Tyr Glu Asp Arg Gln Cys Glu Val Gly
                245                 250                 255
Met Ile Val Gly Thr Gly Cys Asn Ala Cys Tyr Met Glu Glu Met Gln
            260                 265                 270
Asn Val Glu Leu Val Glu Gly Asp Glu Gly Arg Met Cys Val Asn Thr
            275                 280                 285
Glu Trp Gly Ala Phe Gly Asp Ser Gly Glu Leu Asp Glu Phe Leu Leu
        290                 295                 300
Glu Tyr Asp Arg Met Val Asp Glu Ser Ser Ala Asn Pro Gly Gln Gln
305                 310                 315                 320
Leu Tyr Glu Lys Ile Ile Gly Gly Lys Tyr Met Gly Glu Leu Val Arg
                325                 330                 335
Leu Val Leu Leu Lys Leu Val Asp Glu Asn Leu Leu Phe His Gly Glu
            340                 345                 350
Ala Ser Glu Gln Leu Arg Thr Arg Gly Ala Phe Glu Thr Arg Phe Val
            355                 360                 365
Ser Gln Val Glu Ser Asp Ser Gly Asp Arg Lys Gln Ile His Asn Ile
        370                 375                 380
Leu Ser Thr Leu Gly Leu Arg Pro Ser Val Thr Asp Cys Asp Ile Val
385                 390                 395                 400
Arg Arg Ala Cys Glu Ser Val Ser Thr Arg Ala Ala His Met Cys Ser
                405                 410                 415
Ala Gly Leu Ala Gly Val Ile Asn Arg Met Arg Glu Ser Arg Ser Glu
            420                 425                 430
Asp Val Met Arg Ile Thr Val Gly Val Asp Gly Ser Val Tyr Lys Leu
            435                 440                 445
His Pro Ser Phe Lys Glu Arg Phe His Ala Ser Val Arg Arg Leu Thr
        450                 455                 460
Pro Asn Cys Glu Ile Thr Phe Ile Glu Ser Glu Gly Ser Gly Arg
465                 470                 475                 480
Gly Ala Ala Leu Val Ser Ala Val Ala Cys Lys Lys Ala Cys Met Leu
                485                 490                 495
Ala Gln
```

<210> SEQ ID NO 7
<211> LENGTH: 486
<212> TYPE: PRT
<213> ORGANISM: Saccharomyces cerevisiae

<400> SEQUENCE: 7

```
Met Val His Leu Gly Pro Lys Lys Pro Gln Ala Arg Lys Gly Ser Met
1               5                   10                  15
Ala Asp Val Pro Lys Glu Leu Met Asp Glu Ile His Gln Leu Glu Asp
            20                  25                  30
Met Phe Thr Val Asp Ser Glu Thr Leu Arg Lys Val Val Lys His Phe
        35                  40                  45
Ile Asp Glu Leu Asn Lys Gly Leu Thr Lys Lys Gly Val Asn Ile Pro
```

-continued

```
            50                  55                  60
Met Ile Pro Gly Trp Val Met Glu Phe Pro Thr Gly Lys Glu Ser Gly
 65                  70                  75                  80

Asn Tyr Leu Ala Ile Asp Leu Gly Gly Thr Asn Leu Arg Val Val Leu
                 85                  90                  95

Val Lys Leu Ser Gly Asn Arg Thr Phe Asp Thr Thr Gln Ser Lys Tyr
                100                 105                 110

Lys Leu Pro His Asp Met Arg Thr Thr Lys His Gln Glu Glu Leu Trp
                115                 120                 125

Ser Phe Ile Ala Asp Ser Leu Lys Asp Phe Met Val Glu Gln Glu Leu
            130                 135                 140

Leu Asn Thr Lys Asp Thr Leu Pro Leu Gly Phe Thr Phe Ser Tyr Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Val Glu Gly His Asp Val Val Pro Leu Leu
                180                 185                 190

Gln Lys Glu Ile Ser Lys Arg Glu Leu Pro Ile Glu Ile Val Ala Leu
                195                 200                 205

Ile Asn Asp Thr Val Gly Thr Leu Ile Ala Ser Tyr Tyr Thr Asp Pro
210                 215                 220

Glu Thr Lys Met Gly Val Ile Phe Gly Thr Gly Val Asn Gly Ala Phe
225                 230                 235                 240

Tyr Asp Val Cys Ser Asp Ile Glu Lys Leu Glu Gly Lys Leu Ala Asp
                245                 250                 255

Asp Ile Pro Ser Asn Ser Pro Met Ala Ile Asn Cys Glu Tyr Gly Ser
                260                 265                 270

Phe Asp Asn Glu His Leu Val Leu Pro Arg Thr Lys Tyr Asp Val Ala
            275                 280                 285

Val Asp Glu Gln Ser Pro Arg Pro Gly Gln Gln Ala Phe Glu Lys Met
            290                 295                 300

Thr Ser Gly Tyr Tyr Leu Gly Glu Leu Leu Arg Leu Val Leu Leu Glu
305                 310                 315                 320

Leu Asn Glu Lys Gly Leu Met Leu Lys Asp Gln Asp Leu Ser Lys Leu
                325                 330                 335

Lys Gln Pro Tyr Ile Met Asp Thr Ser Tyr Pro Ala Arg Ile Glu Asp
                340                 345                 350

Asp Pro Phe Glu Asn Leu Glu Asp Thr Asp Met Phe Gln Lys Asp
            355                 360                 365

Phe Gly Val Lys Thr Thr Leu Pro Glu Arg Lys Leu Ile Arg Arg Leu
            370                 375                 380

Cys Glu Leu Ile Gly Thr Arg Ala Ala Arg Leu Ala Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Lys Tyr Pro Gly Phe Lys Glu Ala Ala Ala
                420                 425                 430

Lys Gly Leu Arg Asp Ile Tyr Gly Trp Thr Gly Glu Asn Ala Ser Lys
            435                 440                 445

Asp Pro Ile Thr Ile Val Pro Ala Glu Asp Gly Ser Gly Ala Gly Ala
            450                 455                 460

Ala Val Ile Ala Ala Leu Ser Glu Lys Arg Ile Ala Glu Gly Lys Val
465                 470                 475                 480
```

```
Ser Gly Ile Ile Gly Ala
            485

<210> SEQ ID NO 8
<211> LENGTH: 486
<212> TYPE: PRT
<213> ORGANISM: Saccharomyces cerevisiae

<400> SEQUENCE: 8

Met Val His Leu Gly Pro Lys Lys Pro Gln Ala Arg Lys Gly Ser Met
 1               5                  10                  15

Ala Asp Val Pro Lys Glu Leu Met Gln Gln Ile Glu Asn Phe Glu Lys
                20                  25                  30

Ile Phe Thr Val Pro Thr Glu Thr Leu Gln Ala Val Thr Lys His Phe
            35                  40                  45

Ile Ser Glu Leu Glu Lys Gly Leu Ser Lys Lys Gly Gly Asn Ile Pro
        50                  55                  60

Met Ile Pro Gly Trp Val Met Asp Phe Pro Thr Gly Lys Glu Ser Gly
65                  70                  75                  80

Asn Tyr Leu Ala Ile Asp Leu Gly Gly Thr Asn Leu Arg Val Val Leu
                85                  90                  95

Val Lys Leu Gly Gly Asp Arg Thr Phe Asp Thr Gln Ser Lys Tyr
                100                 105                 110

Arg Leu Pro Asp Ala Met Arg Thr Thr Gln Asn Pro Asp Glu Leu Trp
            115                 120                 125

Glu Phe Ile Ala Asp Ser Leu Lys Ala Phe Ile Asp Glu Gln Phe Pro
        130                 135                 140

Gln Gly Ile Ser Glu Pro Ile Pro Leu Gly Phe Thr Phe Ser Tyr Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Val Glu Gly His Asp Val Val Pro Leu Leu
            180                 185                 190

Gln Lys Glu Ile Ser Lys Arg Glu Leu Pro Ile Glu Cys Cys Ala Leu
        195                 200                 205

Ile Asn Asp Thr Thr Gly Thr Leu Val Ala Ser Tyr Tyr Thr Asp Pro
210                 215                 220

Glu Thr Lys Met Gly Val Ile Phe Gly Thr Gly Val Asn Gly Ala Tyr
225                 230                 235                 240

Tyr Asp Val Cys Ser Asp Ile Glu Lys Leu Trp Gly Lys Leu Ser Asp
                245                 250                 255

Asp Ile Pro Pro Ser Ala Pro Met Ala Ile Asn Cys Glu Tyr Gly Ser
            260                 265                 270

Phe Asp Asn Glu His Val Val Leu Pro Arg Thr Lys Tyr Asp Ile Thr
        275                 280                 285

Ile Asp Glu Glu Ser Pro Arg Pro Gly Trp Trp Thr Phe Glu Lys Met
    290                 295                 300

Ser Ser Gly Tyr Tyr Leu Gly Glu Ile Leu Arg Leu Ala Leu Met Asp
305                 310                 315                 320

Met Tyr Lys Gln Gly Phe Ile Phe Lys Asn Gln Asp Leu Ser Lys Phe
                325                 330                 335

Asp Lys Pro Phe Val Met Asp Thr Ser Tyr Pro Ala Arg Ile Glu Glu
            340                 345                 350

Asp Pro Phe Glu Asn Leu Glu Asp Thr Asp Asp Leu Phe Gln Asn Glu
```

-continued

```
            355                 360                 365
Phe Gly Ile Asn Thr Thr Val Gln Glu Arg Lys Leu Ile Arg Arg Leu
            370                 375                 380

Ser Glu Leu Ile Gly Ala Arg Ala Arg Leu Ser Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Arg Tyr Pro Gly Phe Lys Glu Lys Ala Ala
                420                 425                 430

Asn Ala Leu Lys Asp Ile Tyr Gly Trp Thr Gln Thr Ser Leu Asp Asp
                435                 440                 445

Tyr Pro Ile Lys Ile Val Pro Ala Glu Asp Gly Ser Gly Ala Gly Ala
                450                 455                 460

Ala Val Ile Ala Ala Leu Ala Gln Lys Arg Ile Ala Glu Gly Lys Ser
465                 470                 475                 480

Val Gly Ile Ile Gly Ala
                485

<210> SEQ ID NO 9
<211> LENGTH: 485
<212> TYPE: PRT
<213> ORGANISM: Kluveromyces lactis

<400> SEQUENCE: 9

Met Val Arg Leu Gly Pro Lys Lys Pro Ala Arg Lys Gly Ser Met
  1               5                  10                  15

Ala Asp Val Pro Ala Asn Leu Met Glu Gln Ile His Gly Leu Glu Thr
                20                  25                  30

Leu Phe Thr Val Ser Ser Glu Lys Met Arg Ser Ile Val Lys His Phe
            35                  40                  45

Ile Ser Glu Leu Asp Lys Gly Leu Ser Lys Lys Gly Gly Asn Ile Pro
        50                  55                  60

Met Ile Pro Gly Trp Val Val Glu Tyr Pro Thr Gly Lys Glu Thr Gly
 65                 70                  75                  80

Asp Phe Leu Ala Leu Asp Leu Gly Gly Thr Asn Leu Arg Val Val Leu
                85                  90                  95

Val Lys Leu Gly Gly Asn His Asp Phe Asp Tyr Tyr Gln Asn Lys Tyr
                100                 105                 110

Arg Leu Pro Asp His Leu Arg Thr Gly Thr Ser Glu Gln Leu Trp Ser
            115                 120                 125

Phe Ile Ala Lys Cys Leu Lys Glu Phe Val Asp Glu Trp Tyr Pro Asp
        130                 135                 140

Gly Val Ser Glu Pro Leu Pro Leu Gly Phe Thr Phe Ser Tyr Pro Ala
145                 150                 155                 160

Ser Gln Lys Lys Ile Asn Ser Gly Val Leu Gln Arg Trp Thr Lys Gly
                165                 170                 175

Phe Asp Ile Glu Gly Val Glu Gly His Asp Val Val Pro Met Leu Gln
            180                 185                 190

Glu Gln Ile Glu Lys Leu Asn Ile Pro Ile Asn Val Arg Leu Ile
        195                 200                 205

Asn Asp Thr Thr Gly Thr Leu Val Ala Ser Leu Tyr Thr Asp Pro Gln
    210                 215                 220

Thr Lys Met Gly Ile Ile Ile Gly Thr Gly Val Asn Gly Ala Tyr Tyr
225                 230                 235                 240
```

Asp Val Val Ser Gly Ile Glu Lys Leu Glu Gly Leu Pro Glu Asp
            245                 250                 255

Ile Gly Pro Asp Ser Pro Met Ala Ile Asn Cys Glu Tyr Gly Ser Phe
        260                 265                 270

Asp Asn Glu Gly Leu Val Leu Pro Arg Thr Lys Tyr Asp Val Ile Ile
    275                 280                 285

Asp Glu Glu Ser Pro Arg Pro Gly Gln Gln Ala Phe Glu Lys Met Thr
290                 295                 300

Ser Gly Tyr Tyr Leu Gly Glu Ile Met Arg Leu Val Leu Leu Asp Leu
305                 310                 315                 320

Tyr Asp Ser Gly Phe Ile Phe Lys Asp Gln Asp Ile Ser Lys Leu Lys
                325                 330                 335

Glu Ala Tyr Val Met Asp Thr Ser Tyr Pro Ser Lys Ile Glu Asp Asp
            340                 345                 350

Pro Phe Glu Asn Leu Glu Asp Thr Asp Leu Phe Lys Thr Asn Leu
        355                 360                 365

Asn Ile Glu Thr Thr Val Val Glu Arg Lys Leu Ile Arg Lys Leu Ala
    370                 375                 380

Glu Leu Val Gly Thr Arg Ala Ala Arg Leu Thr Val Cys Gly Val Ser
385                 390                 395                 400

Ala Ile Cys Asp Lys Arg Gly Tyr Lys Thr Ala His Ile Ala Ala Asp
                405                 410                 415

Gly Ser Val Phe Asn Arg Tyr Pro Gly Tyr Lys Glu Lys Ala Ala Gln
            420                 425                 430

Ala Leu Lys Asp Ile Tyr Asn Trp Asp Val Glu Lys Met Glu Asp His
        435                 440                 445

Pro Ile Gln Leu Val Ala Ala Glu Asp Gly Ser Gly Val Gly Ala Ala
    450                 455                 460

Ile Ile Ala Cys Leu Thr Trp Lys Arg Leu Ala Ala Gly Lys Ser Val
465                 470                 475                 480

Gly Ile Lys Gly Glu
                485

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
atgggtaaag tagctgtt                                                     18

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
atgggtaaag tggcagttgc aa                                                22

<210> SEQ ID NO 12
<211> LENGTH: 21
<212> TYPE: DNA
<213> ORGANISM: Artificial Sequence
<220> FEATURE:
<223> OTHER INFORMATION: Primer

```
<400> SEQUENCE: 12
ttaagagtct tcaaggtaga g                                      21

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
ttaacttgtt tcagagtcat cttc                                   24
```

PLANT SUGAR SENSORS AND USES THEREOF

STATEMENT AS TO FEDERALLY SPONSORED RESEARCH

This invention was made in part with Government funding, and the Government therefore has certain rights in the invention.

BACKGROUND OF THE INVENTION

This application relates to plant carbohydrate metabolism; in particular, to enzymes which transduce sugar-sensing signals, their encoding genes, and uses thereof.

Sugars are said to be regulatory molecules that are capable of controlling physiology, metabolism, cell cycle, development, and gene expression. Throughout the higher plant life cycle, from germination to flowering to senescence, sugars affect growth and development. Recently, it has become apparent that sugars are physiological signals capable of repressing or activating plant genes that are involved in many essential processes, including photosynthesis, the glyoxylate cycle, respiration, starch and sucrose synthesis and degradation, nitrogen metabolism and storage, pathogen defense, the wounding response, cell cycle progression, pigmentation, and senescence (Sheen, *Photosynthesis Res.* 39, 427 (1994); Thomas and Rodriguez, *Plant Physiol.* 106, 1235 (1994); Knight and Gray, *Mol. Gen. Genet.* 242, 586 (1994); Lam et al., *Plant Physiol.* 106, 1347 (1994); Chen et al., *Plant J.* 6, 625 (1994); Reynolds and Smith, *Plant Mol. Biol.* 29, 885 (1995); Herbers et al., Plant Mol. Biol. 29, 1027 (1995); Mita et al., *Plant Physiol.* 107, 895 (1995)). Studies in a variety of plant species have also shown that sugar homeostasis appears to be tightly regulated. Elevated sugar concentration leads to stunted growth, reduced photosynthesis, leaf curling, chlorosis, necrotic leaves, and anthocyanin accumulation (Casper et al., *Plant Physiol.* 79, 11 (1985); von Schaewen et al., *EMBO J.* 9, 3033 (1990); Dickinson et al., *Plant Physiol.* 95, 420 (1991); Tsukaya et al., Plant Physiol. 97, 1414 (1991); Sonnewald et al., *Plant J.* 1, 95 (1991); Huberet and Hanson, *Plant Physiol.* 99, 1449 (1992); Sonnewald et al., Plant Responses to Sugar Accumulation in Transgenic Tobacco Plants, pp. 246–257, In: M. A. Madore, W. J. Lucas (eds.), *Carbon Partitioning and Source-Sink Interactions in Plants*, American Society of Plant Physiologists, Rockville, Md., (1995)). In addition, environmental factors such as elevated $CO_2$ and intrinsic genetic variations such as different invertase levels have been proposed to affect photosynthetic capacity through sugar regulation (Stitt, *Plant Cell Environ.* 14, 741 (1991); Stitt et al., *Planta* 183, 40 (1991); VanOosten et al., *Plant Cell Environ.* 17, 913 (1994); Nie et al., *Plant Physiol.* 108, 975 (1995); Goldschmidt and Huber, *Plant Physiol.* 99, 1443 (1992)).

SUMMARY OF THE INVENTION

By manipulating the expression of a plant hexokinase protein (HXK), we have discovered that this protein is a sensor that mediates diverse sugar responses in plants. In particular, we have engineered transgenic plants that either: (a) express a decreased level of hexokinase protein due to expression of an antisense hexokinase gene and therefore exhibit a decreased sensitivity to sugar; or (b) express an increased level of hexokinase protein and therefore exhibit an increased sensitivity to sugar. Our discovery has broad implications for the manipulation of agricultural crops, for increasing crop yield and quality, and for reducing production costs.

In general, the invention features a method for reducing the level of a plant hexokinase protein in a transgenic plant cell, the method involving expressing in the transgenic plant cell (for example, a cell from a monocot, a dicot, or a gymnosperm) an antisense hexokinase nucleic acid sequence. This produces transgenic plants that are less sensitive to sugar (for example, glucose, sucrose, fructose, or mannose).

In preferred embodiments, the antisense hexokinase nucleic acid sequence is encoded by a transgene integrated into the genome of the transgenic plant cell; the antisense hexokinase nucleic acid sequence includes a plant antisense hexokinase DNA sequence (for example, a sequence that is based on the AtHXK1 nucleotide sequence of FIG. 1F (SEQ ID NO: 3) or the AtHXK2 nucleotide sequence of FIG. 1G (SEQ ID NO: 4)); and the method further includes growing a transgenic plant from the transgenic plant cell, whereby the level of the hexokinase protein is reduced in the transgenic plant.

In related aspects, the invention features a plant cell (for example, a plant cell from a monocot, dicot, or gymnosperm) expressing an antisense hexokinase nucleic acid sequence; and a plant expression vector including an antisense hexokinase nucleic acid sequence, wherein the sequence is operably linked to an expression control region.

In yet another aspect, the invention features a method for increasing the level of a hexokinase protein in a transgenic plant cell, involving expressing in the transgenic plant cell a hexokinase nucleic acid sequence. In preferred embodiments, the hexokinase nucleic acid sequence is from a plant (for example, a DNA sequence that is identical to the AtHXK1 nucleotide sequence of FIG. 1F (SEQ ID NO: 3) or that is substantially identical to the AtHXK2 nucleic acid sequence of FIG. 1G (SEQ ID NO: 4)). This method produces transgenic plants having an increased sensitivity to sugar.

In related aspects, the invention features a substantially pure plant HXK polypeptide including an amino acid sequence substantially identical to the amino acid sequence of AtHXK1 (SEQ ID NO: 1) or AtHXK2 (SEQ ID NO: 2). In preferred embodiments of both of these aspects, the HXK polypeptide is obtained from a plant including, but not limited to, a monocot (for example, rice, corn, wheat, or barley), a dicot (for example, a member of the Solanaceae (for example, potatoes) or a member of the Cruciferae (for example, Arabidopsis, broccoli, cabbage, brussel sprouts, rapeseed, kale, Chinese kale, cauliflower, or horseradish)), and a gymnosperm.

In yet other related aspects, the invention features a substantially pure DNA encoding a plant HXK polypeptide that includes an amino acid sequence substantially identical to the amino acid sequence of AtHXK1 (SEQ ID NO: 1) or AtHXK2 (SEQ ID NO: 2). In preferred embodiments, the DNA includes the nucleotide sequence shown in FIG. 1F (SEQ ID NO: 3) or includes a nucleotide sequence that is substantially identical to the sequence that is shown in FIG. 1G (SEQ ID NO: 4). Such DNAs are obtained from any plant including, but not limited to, a monocot (for example, rice, corn, wheat, and barley), a dicot (for example, a member of the Solanaceae (for example, potatoes) or a member of the Cruciferae (for example, Arabidopsis, broccoli, cabbage, brussel sprouts, rapeseed, kale, Chinese kale, cauliflower, or horseradish)), and a gymnosperm. In other preferred embodiments, the DNAs of the invention are operably linked to a constitutive or regulated promoter.

In yet other related aspects, the invention features a vector including any of the substantially pure DNAs of the invention, the vector being capable of directing expression of the protein encoded by the DNA in a vector-containing cell; a cell, for example, a prokaryotic cell (for example, an *E. coli* cell) or a eukaryotic cell (for example, a plant cell) which includes any of the DNAs of the invention; and a transgenic plant (or a cell or a seed derived from such a transgenic plant) including any of the DNAs of the invention integrated into the genome of the plant, wherein the DNA is expressed in the transgenic plant.

In various preferred embodiments, the plant cell contains the DNA in the sense orientation and has an increased sensitivity to sugar; the plant cell contains the DNA in the antisense orientation and is less sensitive to sugar; and the DNA is expressed under the control of a constitutive promoter or regulated promoters.

In two other aspects, the invention features a method of producing a plant HXK polypeptide involving: (a) providing a cell transformed with a gene encoding a polypeptide including either an amino acid sequence substantially identical to the amino acid sequence of AtHXK1 (SEQ ID NO: 1) or an amino acid sequence substantially identical to the amino acid sequence of AtHXK2 (SEQ ID NO: 2) positioned for expression in the cell; (b) expressing the plant HXK polypeptide; and (c) recovering the plant HXK polypeptide.

By "hexokinase" or "HXK" is meant a polypeptide that is capable of catalyzing the ATP-dependent conversion of hexoses to hexose-6-phosphates. Methods for assaying such enzymatic activities are known in the art, e.g., those described herein by Renz and Stitt (*Planta* 190, 166 (1993)).

By "reducing the level of a plant hexokinase protein" is meant a decrease in the level of that plant hexokinase protein by at least 30–50%, preferably by 50–80%, and more preferably by 80–95% relative to the level in a control plant (for example, a wild-type plant). Reduction of hexokinase protein levels may be accomplished through the expression of an antisense plant hexokinase nucleotide sequence in a transgenic plant. Levels of plant hexokinase protein are monitored according to any standard technique including, but not limited to, immunoblotting (for example, as described herein). Alternatively, the level of a plant hexokinase protein may be quantified according to standard hexose phosphorylation assays (for example, those described herein).

By "increasing the level of a plant hexokinase protein" is meant increasing the level of that plant hexokinase protein by at least 50%, preferably 100%, and more preferably greater than 200% relative to the level in a control plant (for example, a wild-type plant). Levels of plant hexokinase protein are monitored according to any standard technique including, but not limited to, immunoblotting (for example, as described herein). Alternatively, the level of a plant hexokinase protein may be quantified according to standard hexose phosphorylation assays (for example, those described herein).

By "an antisense hexokinase sequence" is meant a nucleotide sequence that is complementary to a plant hexokinase messenger RNA. In general, such an antisense sequence will usually be at least 15 nucleotides, preferably about 15–200 nucleotides, and more preferably 200–2,000 nucleotides in length. The antisense sequence may be complementary to all or a portion of the plant hexokinase mRNA nucleotide sequence (for example, the AtHXK1 and AtHXK2 antisense constructs described herein), and, as appreciated by those skilled in the art, the particular site or sites to which the antisense sequence binds as well as the length of the antisense sequence will vary, depending upon the degree of inhibition desired and the uniqueness of the antisense sequence. A transcriptional construct expressing a plant hexokinase antisense nucleotide sequence includes, in the direction of transcription, a promoter, the sequence coding for the antisense RNA on the sense strand, and a transcriptional termination region. Antisense HXK sequences may be constructed and expressed as described herein or as described, for example, in van der Krol et al., *Gene* 72, 45 (1988); Rodermel et al., *Cell* 55, 673 (1988); Mol et al., *FEBS Lett.* 268, 427 (1990); Weigel and Nilsson, *Nature* 377, 495 (1995); Cheung et al., *Cell* 82, 383 (1995); and U.S. Pat. No. 5,107,065.

By "less sensitive to sugar" is meant that the developmental, physiological, or molecular processes that are typically regulated or controlled by internal or external sugar concentrations exhibit reduced responses to the presence of a sugar (for example, glucose, fructose, mannose, or sucrose). For example, a plant having reduced sensitivity to sugar is capable of activating an assortment of genes (for example, photosynthetic genes) that are normally repressed by the presence of sugar, or such a plant is capable of proceeding through its normal developmental pathway even in the presence of sugar concentrations that would otherwise thwart or prevent such development. Analysis of a plant's sensitivity to sugar is accomplished using a wide variety of bioassays (for example, those described herein). These assays include, but are not limited to, evaluating and monitoring gene expression, seed germination, cotyledon development (for example, cotyledon extension), cotyledon greening, leaf development, embryonic root development, hypocotyl elongation, anthocyanin accumulation, starch accumulation, and time needed for flowering. By comparing phenotypes of wild-type plants and candidate plants (for example, a plant expressing an antisense hexokinase gene), one is readily able to determine whether such a candidate transgenic plant has a reduced sensitivity to a sugar. For example, sugars have been found to repress the expression of both photosynthetic (for example, ribulose bisphosphate carboxylase small subunit and light-harvesting chlorophyll a/b binding protein) and non-photosynthetic (for example, α-amylase, sucrose synthase, malate synthase, and asparagine synthase) genes. Thus, in plants that are less sensitive to sugar, the aforementioned sugar-repressible genes have a decreased, reduced, or attenuated level of sugar-mediated repression.

By "increased sensitivity" is meant that the developmental, physiological, or molecular processes that are typically regulated or controlled by internal or external sugar concentrations exhibit increased or elevated responses to the presence of a sugar (for example, glucose, fructose, mannose, or sucrose). For example, a plant having increased sensitivity to sugar is capable of elevating, raising, or promoting the activation of an assortment of genes (for example, vegetative storage proteins) that are normally activated by the presence of sugar. Analysis of a plant's sensitivity to sugar is accomplished using a wide variety of bioassays. These assays include, but are not limited to, evaluating and monitoring gene expression, seed germination, cotyledon development (for example, cotyledon extension), cotyledon greening, leaf development, embryonic root development, hypocotyl elongation, anthocyanin accumulation, starch accumulation, and time needed for flowering. By comparing phenotypes of wild-type plants and candidate plants (for example, a plant expressing at least one additional copy of hexokinase gene), one is readily able to determine whether such a candidate transgenic plant has an increased sensitivity to a sugar. For example, sugars have been found to activate the expression of genes such as nitrate reductase, β-amylase, sucrose synthase, and potato storage protein. Thus, in plants exhibiting an increased sensitivity to sugar, the aforementioned sugar-inducible genes have an increased, elevated, or heightened level of sugar-mediated expression.

By "polypeptide" or "protein" is meant any chain of amino acids, regardless of length or post-translational modification (for example, glycosylation or phosphorylation).

By "substantially identical to AtHXK1" is meant a plant hexokinase polypeptide that includes an N-terminus which is at least 50%, preferably 75%, more preferably 85–90%, and most preferably 95% identical to the N-terminus of AtHXK1 (amino acids 1–61 of FIG. 1B; SEQ ID NO:1). The length of comparison will generally be at least 15 amino acids, preferably at least 30 amino acids, more preferably at least 40 amino acids, and most preferably 60 amino acids.

By "substantially identical to AtHXK2" is meant a plant hexokinase polypeptide or nucleic acid sequence that exhibits at least 86%, preferably 90%, more preferably 95%, and most preferably 99% identity to the amino acid or nucleic acid sequences of AtHXK2 (FIGS. 1B and 1G; SEQ ID NOS: 2 and 4).

Sequence identity is typically measured using sequence analysis software (for example, Sequence Analysis Software Package of the Genetics Computer Group (University of Wisconsin Biotechnology Center, 1710 University Avenue, Madison, Wis. 53705), BLAST, or PILEUP/PRETTYBOX programs). Such software matches similar sequences by assigning degrees of homology to various substitutions, deletions, substitutions, and other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

By a "substantially pure polypeptide" is meant a plant hexokinase polypeptide (for example, AtHXK1 or AtHXK2) which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, plant hexokinase polypeptide. A substantially pure plant hexokinase polypeptide may be obtained, for example, by extraction from a natural source (for example, a plant cell); by expression of a recombinant nucleic acid encoding a plant hexokinase polypeptide; or by chemically synthesizing the protein. Purity can be measured by any appropriate method, for example, column chromatography, polyacrylamide gel electrophoresis, or HPLC analysis.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (for example, a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) an HXK polypeptide (for example, AtHXK1 or AtHXK2).

By "positioned for expression" is meant that the DNA molecule is positioned adjacent to a DNA sequence which directs transcription and translation of the sequence (i.e., facilitates the production of, for example, a plant hexokinase polypeptide such as AtHXK1 or AtHXK2, a recombinant protein, or a RNA molecule).

By "promoter" is meant a minimal sequence sufficient to direct transcription. Included in the invention are promoter elements that are sufficient to render promoter-dependent gene expression controllable for cell-, tissue-, or organ-specific gene expression, or elements that are inducible by external signals or agents (for example, light-, pathogen-, wound-, or hormone-inducible elements); such elements may be located in the 5' or 3' regions of the native gene.

By "operably linked" is meant that a gene and a regulatory sequence(s) are connected in such a way as to permit gene expression when the appropriate molecules (for example, transcriptional activator proteins) are bound to the regulatory sequence(s).

By "plant cell" is meant any self-propagating cell bounded by a semi-permeable membrane and containing a plastid. Such a cell also requires a cell wall if further propagation is desired. Plant cell, as used herein includes, without limitation, algae, cyanobacteria, seeds, suspension cultures, embryos, meristematic regions, callus tissue, leaves, roots, shoots, gametophytes, sporophytes, pollen, and microspores.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic plants and the DNA (transgene) is inserted by artifice into the nuclear or plastidic genomes.

Other features and advantages of the invention will be apparent from the following description of the preferred embodiments thereof, and from the claims.

DETAILED DESCRIPTION

The drawings will first be described.

DRAWINGS

FIGS. 1A–E are illustrations showing various aspects of the molecular characterization of the *Arabidopsis thaliana* HXK genes. FIG. 1A shows the functional complementation HXK catalytic activity using a yeast hxk1/hxk2 double mutant (designated DBY2219) with the *A. thaliana* HXK homologues, AtHXK1 and AtHXK2. pFL61 is shown as the control vector used in these complementation studies. FIGS. 1B-1, 1B-2, and 1B-3 are schematic illustrations showing the amino acid sequence comparison of *A. thaliana* hexokinase AtHXK1 (SEQ ID NO: 1), *A. thaliana* hexokinase AtHXK2 (SEQ ID NO: 2), human GLK (SEQ ID NO: 5), rat GLK (SEQ ID NO: 6), *Saccharomyces cerevisiae* HXK1

(Yeast1) (SEQ ID NO: 7), *S. cerevisiae* HXK2 (Yeast2) (SEQ ID NO: 8), and *Kluveromyces lactis* RAG5 (Yeast3) (SEQ ID NO: 9). The underlined regions 1 and 2 refer to the conserved phosphate 1 and 2 regions; the underlined dashed region refers to the adenosine interaction region. Amino acids which are underlined with asterisks refer to the conserved sugar binding domain. Sequence analysis was performed using the PILEUP/PRETTYBOX program set to standard parameters. Identical and similar residues are referred to as boxed and highlighted regions, respectively. FIG. 1C is a schematic illustration showing the map positions of AtHXK1 and AtHXK2 on Arabidopsis chromosomes IV and II, respectively. FIG. 1D is a photograph of a DNA blot analysis showing that AtHXK is encoded by a multigene family. The blots were hybridized with a full-length cDNA probe of AtHXK1 (designated AtHXK1, shown on the left) or AtHXK2 (designated AtHXK2, shown on the right). Numbers indicated on the left of the blots refer to the molecular size markers in kilobases. FIG. 1E is a photograph of a DNA blot analysis of *A. thaliana* genomic DNA which was digested with HindIII, fractionated by gel electrophoresis, transferred to a nylon membrane, and hybridized with the AtHXK1 full-length cDNA probe under low stringency conditions.

Figure 2A:
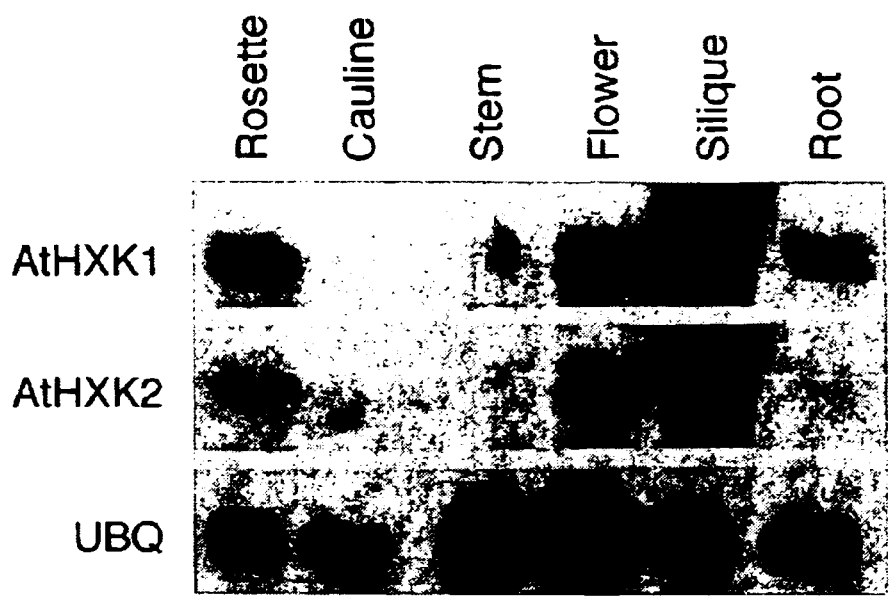
Figure 2B:
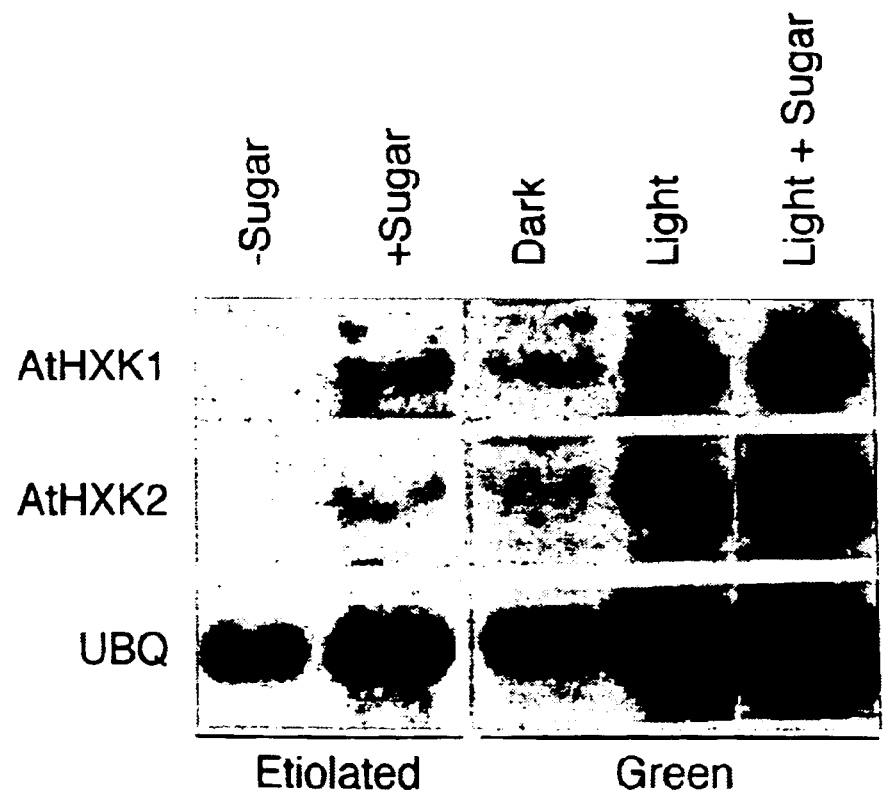

FIGS. 2A–B are a series of illustrations showing HXK expression in Arabidopsis. FIG. 2A is a photograph of an RNA blot showing the expression of AtHXK1 and AtHXK2 in leaf (rosette and cauline), stem, flower, silique, and root tissues. FIG. 2B is a photograph of an RNA blot showing that the expression of AtHXK1 and AtHXK2 is induced by light and sugar.

Figure 3A:
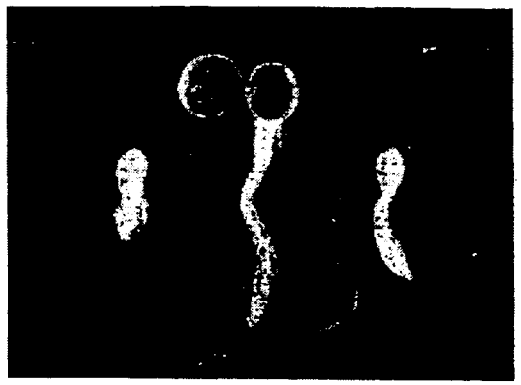
Figure 3B:
Figure 3C:
Figure 3D:
Figure 3E:
Figure 3F:

FIGS. 3A–F are color photographs of Arabidopsis seedlings illustrating HXK as a sugar sensor in plants. FIG. 3A is a photograph of transgenic Arabidopsis seedlings which were germinated on 1/2 MS plates containing 6% glucose and which have increased expression of either sense-AtHXK1 (left) or anti-AtHXK1 (middle) constructs. A wild-type (control) plant is shown on the right. FIG. 3B is a photograph of transgenic Arabidopsis seedlings which were germinated on 1/2 MS plates containing 0.8 mM 2-dGlc and which have increased expression of either sense-AtHXK1 (left) or anti-AtHXK1 (middle) constructs. A wild-type (control) plant is shown on the right. FIG. 3C is a photograph showing a T3 homozygous population of sense-AtHXK1 (left) and anti-AtHXK1 (right) plants which were germinated on 1/2 MS plates containing 6% glucose. FIG. 3D is a photograph showing a T3 homozygous population of sense-AtHXK1 (left) and anti-AtHXK1 (right) plants which were germinated on 1/2 MS plates containing 0.8 mM 2-dGlc. FIG. 3E is a photograph showing sense-AtHXK1 (left), anti-AtHXK1 (middle), and control (right) plants which were germinated on 1/2 MS plates containing 6% mannitol. FIG. 3F is a photograph showing sense-AtHXK1 (left), anti-AtHXK1 (middle), and control (right) plants which were germinated on 1/2 MS plates containing 6% 3-MeGlc.

Figure 4C:
Figure 4B:
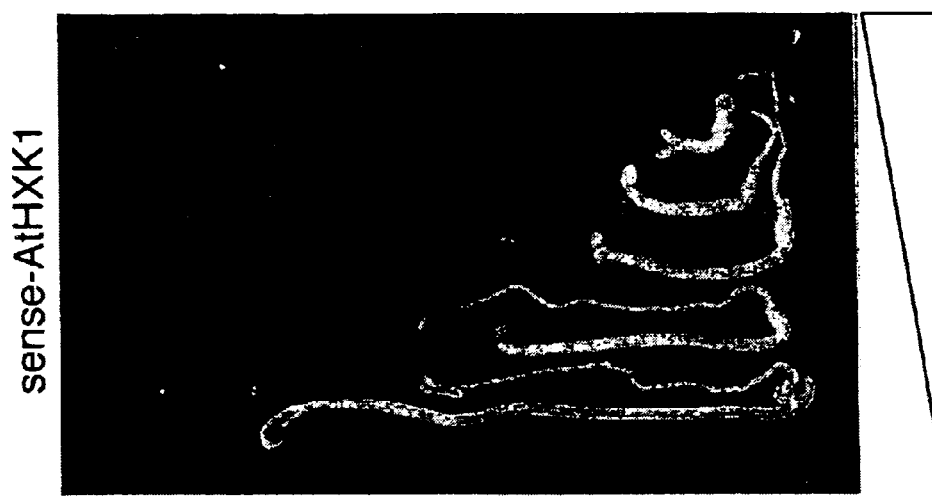
Figure 4A:
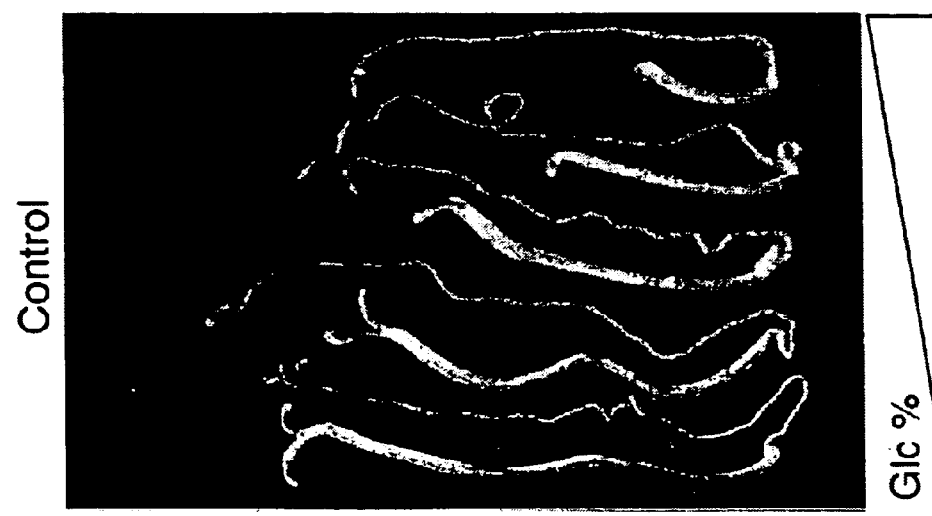

FIGS. 4A–C are a series of color photographs showing that AtHXK mediates sugar effects on seedling growth and development. Seedlings were grown in the dark for 6 days followed by illumination for 12 hours, on media containing various glucose concentrations (shown as increasing concentrations of glucose (Glc %) 2, 3, 4, 5, or 6%). FIG. 4A is a photograph showing that higher concentrations of glucose inhibit hypocotyl elongation and expansion as well as greening of cotyledons in wild-type (control) plants. FIG. 4B is a photograph of sense-AtHXK1 plants that are hypersensitive to glucose as indicated by the strong inhibitory effects on seedling development. FIG. 4C is a photograph of anti-AtHXK1 plants that are less sensitive to glucose as shown by decreased inhibitory effects on seedling development when compared to wild-type plants.

Figure 5A:
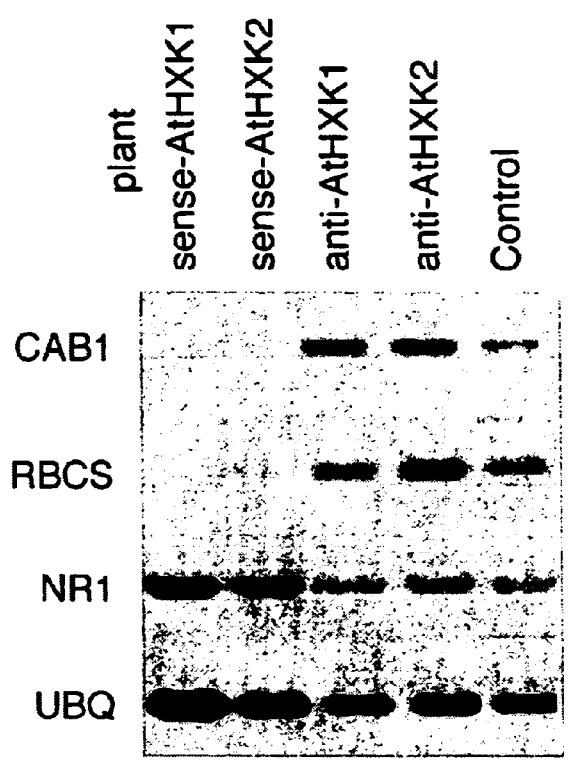
Figure 5B:
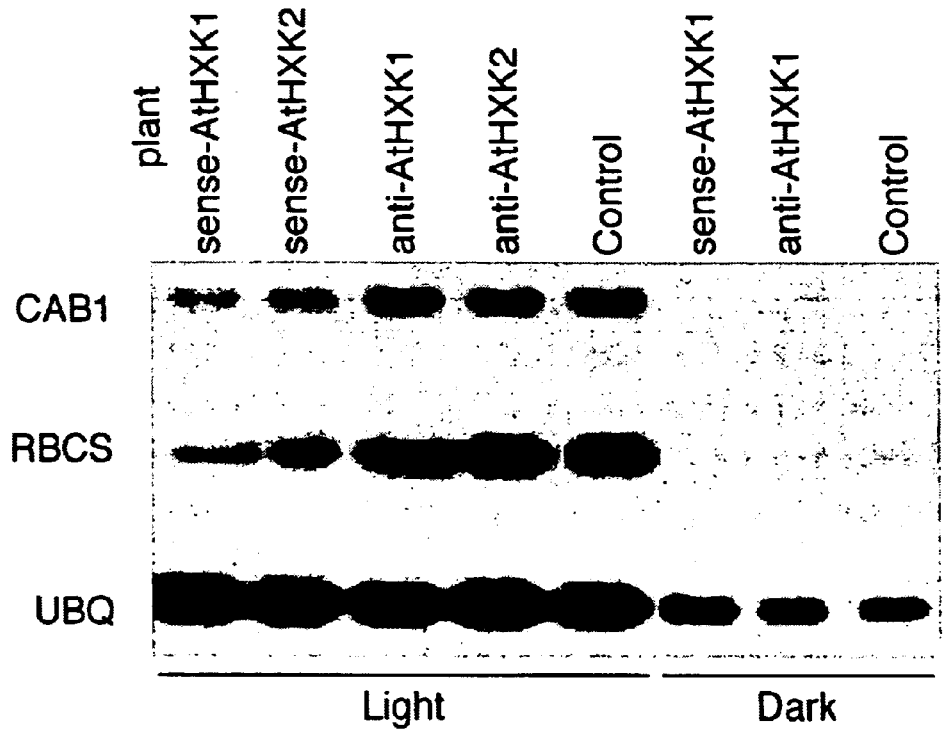
Figure 5C:
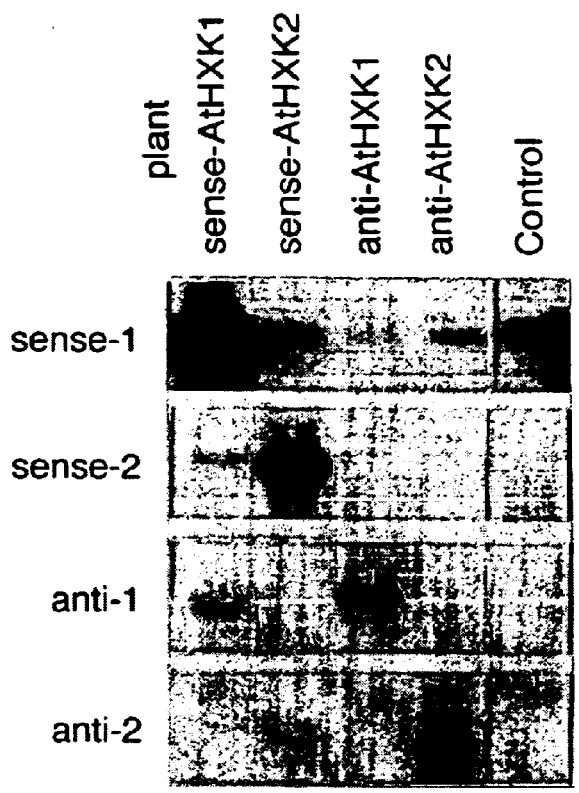
Figure 5D:
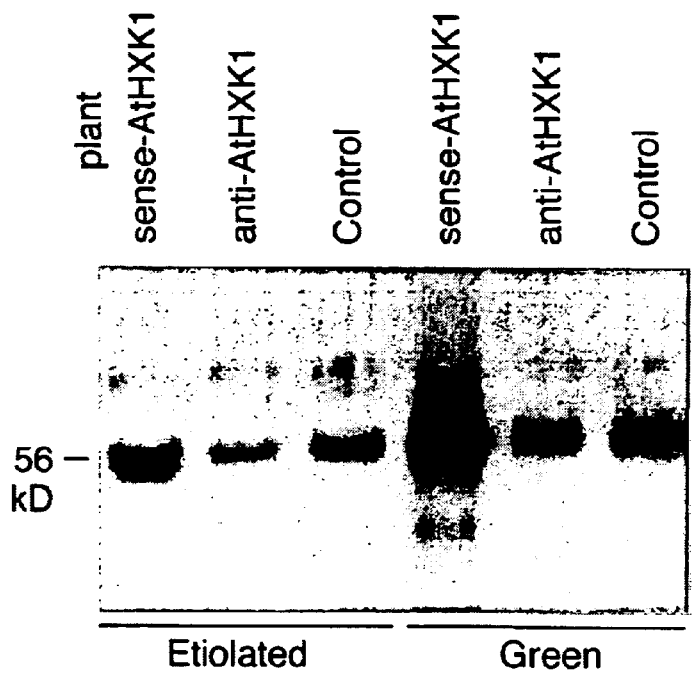

FIGS. 5A–F are a series of illustrations showing the expression of various genes in control, sense-, and anti-sense plants. FIG. 5A is a photograph of an RNA blot analysis using illuminated etiolated seedlings which were germinated on 1/2 MS plates containing 6% glucose. UBQ expression was monitored as a control. FIG. 5B is a photograph of an RNA blot analysis of RNA prepared from light-grown green plants (Light) which were propagated without exogenous sugars, and from light-grown green plants (Dark) which were dark adapted for 3 days and then illuminated for 4 hours. FIG. 5C is a photograph of several RNA blots showing the expression of sense and antisense constructs in the transgenic plants. RNAs were extracted from etiolated seedlings grown on 1/2 MS plates containing 6% glucose. Gene- and strand-specific probes were used to reveal sense-AtHXK1 (sense-1), sense-AtHXK2 (sense-2), antisense-AtHXK1 (anti-1), and antisense-AtHXK2 (anti-2) transcripts. The blot that shows sense-AtHXK1 (sense-1) expression was exposed for a longer period of time than the other blots. Wild-type plants were used as controls. FIG. 5D is a photograph of a protein blot analysis showing the expression of AtHXK1. Sense-AtHXK1 plants showed elevated expression of AtHXK1, and anti-AtHXK1 plants showed reduced expression. Wild-type plants were used as controls.

Figure 5E:
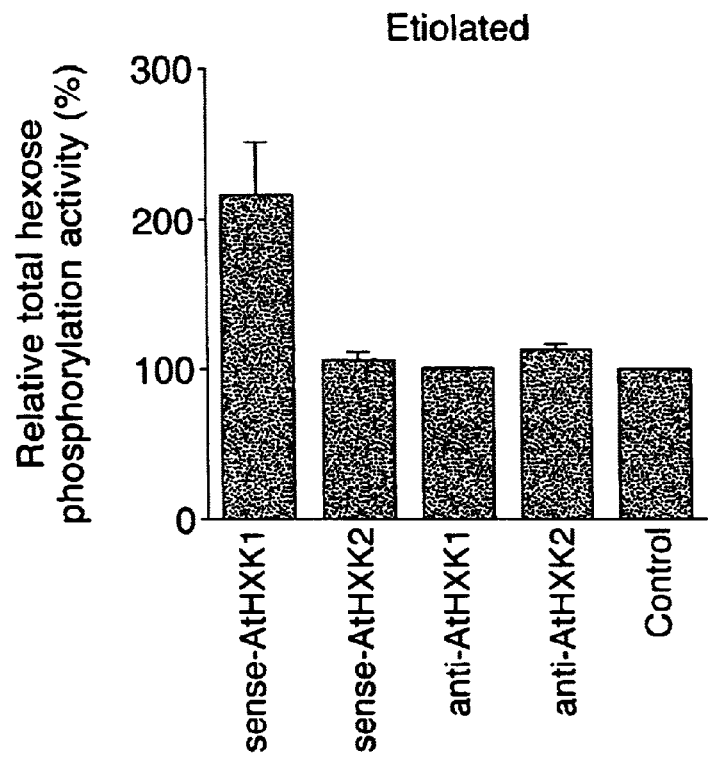
Figure 5F:
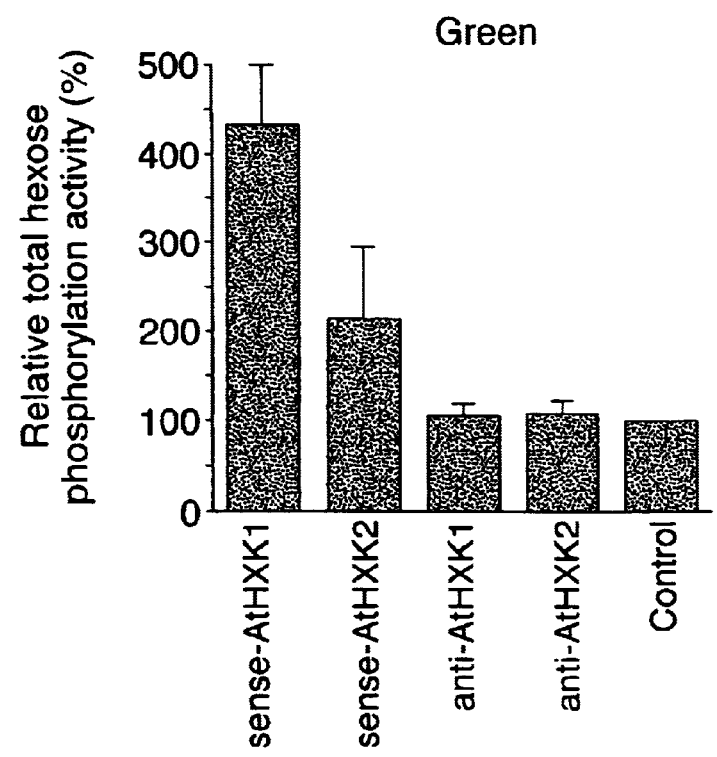

FIG. 5E is a bar graph showing the total hexose phosphorylation activities in etiolated seedlings expressing sense-AtHXK1, sense AtHXK2, anti-AtHXK1, anti-AtHXK2, and control constructs. FIG. 5F is a bar graph showing the total hexose phosphorylation activities in light grown plants expressing sense-AtHXK1, sense AtHXK2, anti-AtHXK1, anti-AtHXK2, and control constructs. Error bars show standard deviations.

Figure 6A:
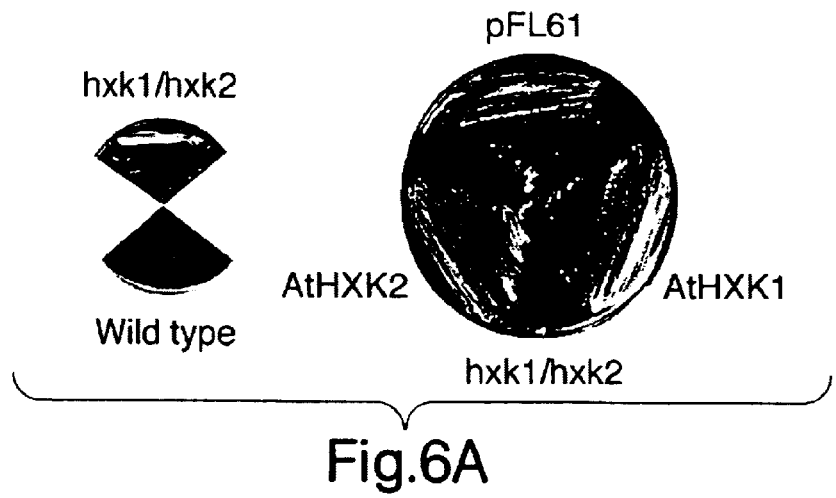
Figure 6B:
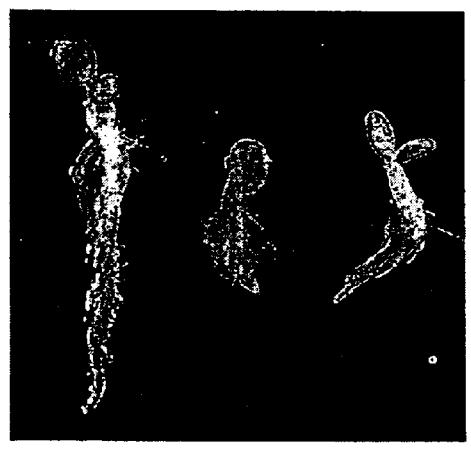
Figure 6C:
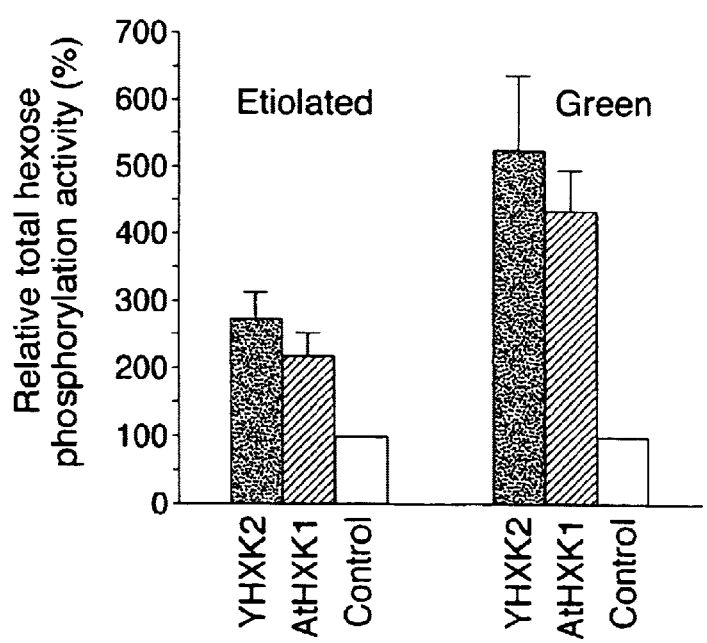

FIGS. 6A–C are a series of illustrations showing that sugar signaling is uncoupled from sugar metabolism. Shown in FIG. 6A are photographs demonstrating that the growth of the wild-type strain, but not the double mutant hxk1/hxk2, is inhibited on a 2-dGlc/raffinose plate (left). Increased expression of either AtHXK1 or AtHXK2 in the hxk1/hxk2 strain did not restore glucose repression, as shown by a level of growth for this strain on a 2-dGlc/raffinose plate which was similar to the double mutant transformed with vector (pFL61) alone (right). FIG. 6B is a color photograph showing the dominant interfering effect of increasing the expression yeast HXK2 in transgenic Arabidopsis seedlings (i.e., YHXK2 plants) which were grown for 7 days on 1/2 MS plates containing 6% glucose. FIG. 6C is a bar graph showing total hexose phosphorylation activities in etiolated or green YHXK2, sense-AtHXK1, and control plants. Error bars represent standard deviations.

There now follows a description of the cloning and characterization of two Arabidopsis HXK-encoding cDNAs which are useful in the instant invention, and a characterization of their ability to regulate sugar metabolism. These examples are provided for the purpose of illustrating the invention, and should not be construed as limiting.

Molecular Characterization of Arabidopsis HXK Genes

Figure 1A:
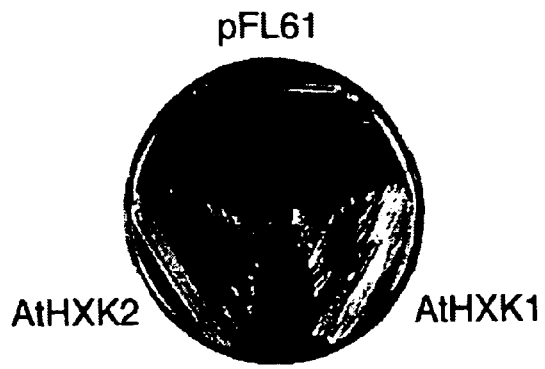
FIG. 1F is an illustration showing the nucleotide sequence of AtHXK1 (SEQ ID NO: 3).
FIG. 1G is an illustration showing the nucleotide sequence of AtHXK2 (SEQ ID NO: 4).

To elucidate the role of HXK as a sugar sensor, the Arabidopsis HXK genes were cloned by functional complementation using a yeast *Saccharomyces cerevisiae* hxk1/hxk2 double mutant (designated DBY2219), a strain which lacked HXK activity (Ma and Botstein, Mol. *Cell. Biol.* 6, 4046 (1986)). Using this approach, we identified two cDNAs, designated AtHXK1 (FIG. 1F; SEQ ID NO: 3, GenBank accession no. U28214) and AtHXK2 (FIG. 1G; SEQ ID NO: 4, GenBank accession no. U28215). These cDNAs, which were 2.0 and 1.9 kb in length respectively, were both found reproducibly to complement the yeast double mutant and to allow its growth on a selection plate containing fructose as the sole carbon source. Exemplary results are shown in FIG. 1A; mutant yeast cells transformed with either the AtHXK1 or AtHXK2 cDNAs were capable of growth on the selection media, indicating that these genes complemented the double mutant. In contrast, mutants transformed with the plasmid vector pFL61 alone were incapable of growth on the same selection media (FIG. 1A) (Minet et al., *Plant J.* 2, 417 (1992)).

DNA sequence analyses of AtHXK1 (FIG. 1F, SEQ ID NO: 3) and AtHXK2 (FIG. 1F, SEQ ID NO: 4) predicted open reading frames of 496 and 502 amino acids, respectively (FIGS. 1B-1, 1B-2, and 1B-3). These genes were found to share 82% nucleotide identity and 85% amino acid identity. In addition, database searches and sequence comparisons revealed that these AtHXKs shared between 34–35% sequence identity with the human and rat GLKs (Nishi et al., *Diabetologia* 35, 743 (1992); Magnuson et al., *Proc. Natl. Acad. Sci. U.S.A.* 86, 4838 (1989)), and between 36–38% sequence identity with several yeast HXKs (Stachelek et al., *Nucl. Acids Res.* 14, 945 (1986); Prior et al., *Mol. Cell. Biol.* 13, 3882. (1993)). Conserved ATP- and sugar-binding domains were also identified in the predicted amino acid sequences of both AtHXK genes. As shown in FIG. 1B, three domains were identified which are involved in ATP binding (Bork et al., *Protein Sci.* 2, 31 (1993)). Also shown in FIG. 1B is a sugar binding domain which is similar to the glucose binding site found in mammalian GLK (Bork et al., *Protein Sci.* 2, 31 (1993)). In general, our sequence comparison revealed that the overall sequence and structure of the Arabidopsis HXKs were similar to those of the mammalian GLK and yeast HXKs, but distinct from that of plant fructokinase (Smith et al., *Plant Physiol.* 102, 1043 (1993)).

Figure 1C:
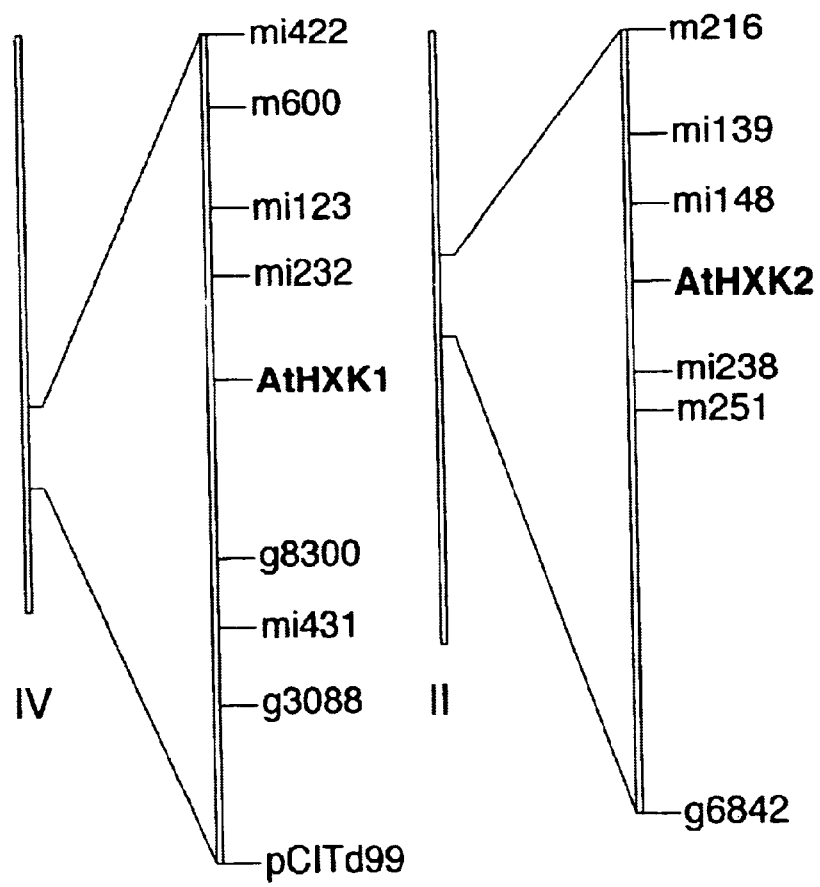
Figure 1B-2:
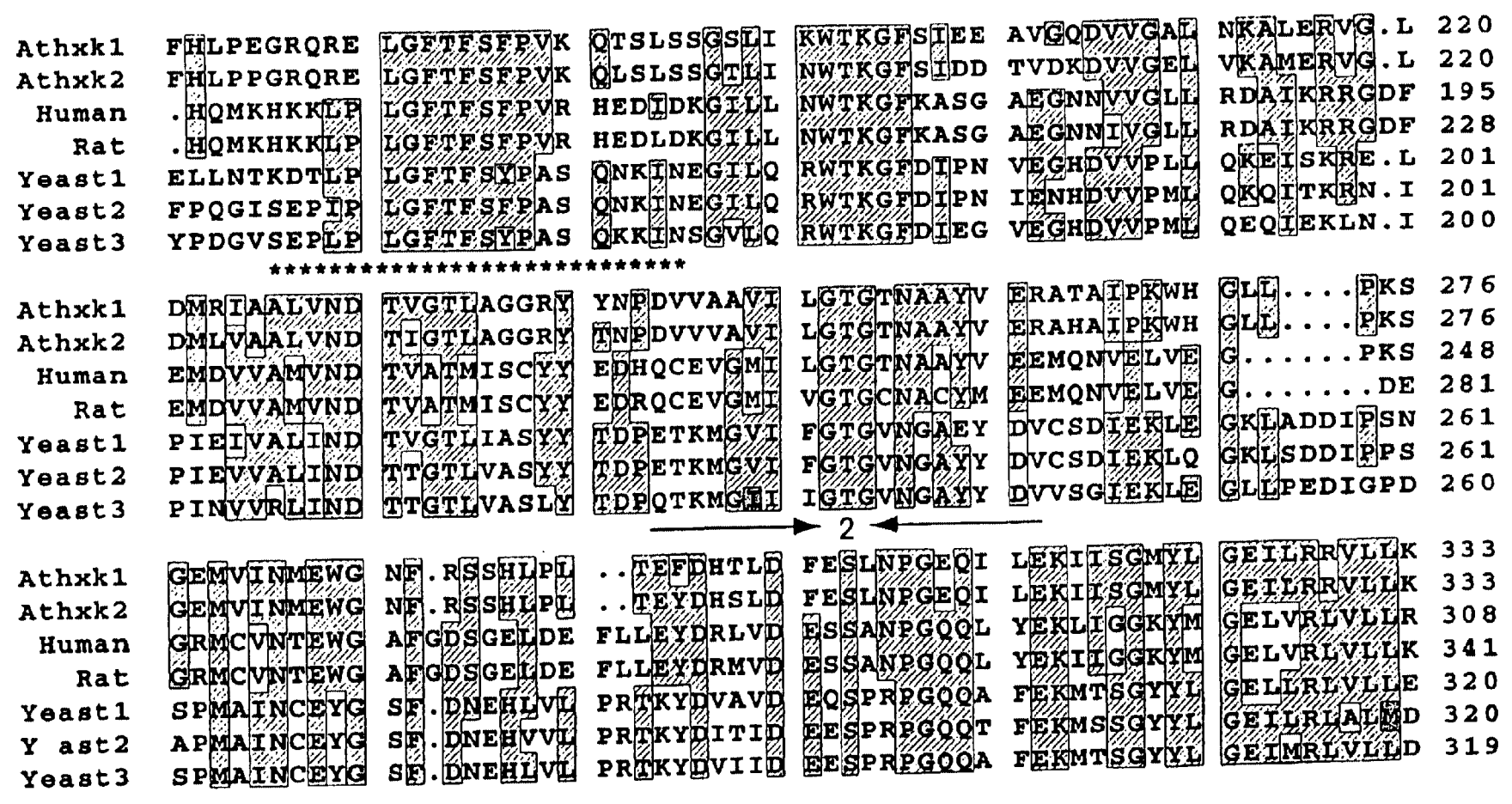

We next determined the chromosomal positions of AtHXK1 and AtHXK2 genes by standard segregation analysis of restriction fragment length polymorphisms (RFLPs) in recombinant inbred lines (Nam et al., *Plant Cell* 1, 699 (1989); Lister and Dean, *Plant J.* 4, 745 (1993); Hauge et al., *Plant J.* 3, 745 (1993); Schmidt et al., *Science* 270, 480 (1995); Zachgo et al., *Genomic Res.* 6, 19 (1996)). By this analysis, we found that AtHXK1 is located on chromosome 4 and is flanked by the chromosomal markers mi232 and g8300 (FIG. 1C), and that AtHXK2 is located on chromosome 2 and is flanked by the chromosomal markers mi148 and mi238 (FIG. 1C).

Figure 1D:
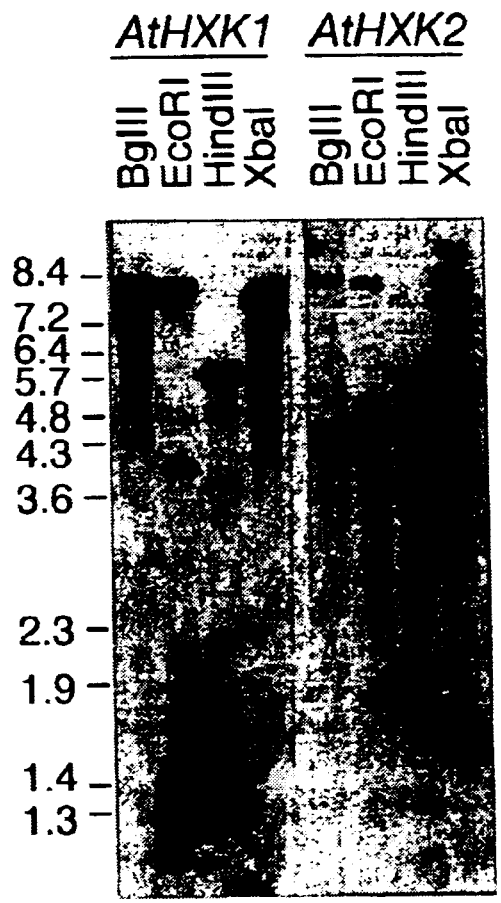
Figure 1E:
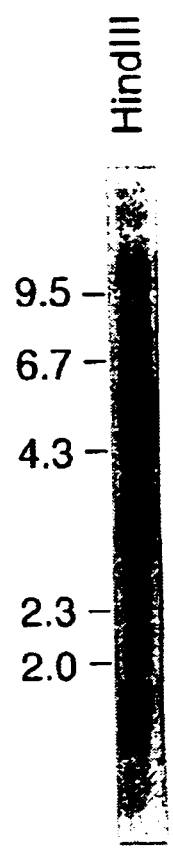

The copy number of the AtHXK genes was determined by genomic DNA (Southern) blot analysis. Genomic DNA was prepared according to standard methods from *A. thaliana* (Landsberg er), digested with BglII, EcoRI, HindIII, or XbaI, fractionated by gel electrophoresis, transferred to a nylon membrane, and hybridized with a full-length cDNA randomly-primed probe of either AtHXK1 or AtHXK2 (Ausubel et al., infra). Genomic DNA blot analysis revealed that AtHXK1 hybridized at high stringency with two DNA fragments which corresponded to the two AtHXK genes (FIG. 1D, blot designated AtHXK1). In addition, at least one other fragment was visible on the same blot when AtHXK2 was used as a probe under identical hybridization conditions (FIG. 1D, blot designated AtHXK2). Using this same approach, a third cDNA (AtHXK3) was also identified, further supporting the hypothesis that three homologous HXK genes exist in Arabidopsis. At low stringency conditions, a large number of additional bands were also detected, suggesting that more than three genes share sequence similarity with AtHXK1 (FIG. 1E).

AtHXK Gene Expression

To examine AtHXK gene expression, RNA blot experiments were performed as follows. RNA was extracted from rosette leaves, cauline leaves, stems, flowers, siliques, and roots according to standard methods. The extracted RNAs were gel fractionated and transferred to a nylon membrane (for example, as described in Ausubel et al., infra). Blots were subsequently hybridized with either AtHXK1, AtHXK2, or ubiquitin (UBQ) probes (Greenberg et al., *Cell* 77, 551 (1994)) according to standard techniques. The UBQ probe was used as a control in these experiments. Equal amounts of RNA were loaded in each lane.

RNA blot analyses indicated that both AtHXK1 and AtHXK2 probes detected RNA bands of approximately 2 kb in length. As shown in FIG. 2A, the transcript levels of both AtHXK1 and AtHXK2 were greatest in the siliques, moderate in flowers and rosette leaves, and lowest in the stem and cauline leaves. In roots, AtHXK1 expression was greater than AtHXK2. The varied levels of AtHXK1 and AtHXK2 expression may reflect their diverse physiological roles, for example, feedback regulation of photosynthesis in source tissues (i.e., sugar providers) such as rosette leaves, and sugar metabolism in sink tissues (i.e., sugar acceptors) such as siliques and flowers.

Since light is required for plants to produce sugars by photosynthesis, we investigated the effect of light on AtHXK gene expression. RNA blot analyses were carried out as described above using total RNA prepared from dark-grown etiolated and light-grown dark-adapted wild-type plants, with or without illumination (designated in FIG. 2B as Dark and Light, respectively). In particular, dark-grown etiolated seedlings were germinated and grown on plates containing 1/2 Murashige-Skoog (MS) medium, with or without 6% glucose (designated in FIG. 2B as +Sugar and −Sugar, respectively). Plants were grown in the dark for 6 days and then exposed to white light (120 $\mu$E m$^{-1}$s$^{-1}$) for 4 hours. Light-grown, dark-adapted plants consisted of fifteen-day-old light-grown green plants which were dark-adapted for 3 days and remained in the dark, or were illuminated and then flushed with 3% glucose (designated in FIG. 2B as Light+Sugar). Growth conditions were as described by Cheng et al. (*Proc. Natl. Acad. Sci., U.S.A.* 89, 1861 (1992)).

As shown in FIG. 2B, both AtHXK1 and AtHXK2 were found to be expressed at very low levels in non-photosynthetic etiolated seedlings, even after 4 hours of illumination. However, their expression was induced by the addition of exogenous sugar. The transcript levels of both AtHXK1 and AtHXK2 were low in dark-adapted green plants, but was induced significantly upon illumination and further enhanced by sugar (FIG. 2B). UBQ gene expression was found to be affected by both light and sugar. These results revealed that AtHXK expression was tied to the conditions in which sugar-sensing and metabolism were needed, indicating that plant sugar homeostasis was controlled by AtHXK levels through an autoregulatory mechanism.

AtHXK as a Suaar Sensor in Plants

To test the hypothesis that AtHXKs act as sugar sensors in intact plants, transgenic plant models were established by introducing sense and antisense genes to alter AtHXK levels. Wild-type (Bensheim) Arabidopsis plants were transformed with binary vectors carrying gene fusions with the CaMV35S promoter and sense AtHXK1 (sense-AtHXK1), sense AtHXK2 (sense-AtHXK2), antisense AtHXK1 (anti-AtHXK1), or antisense AtHXK2 (anti-AtHXK2) using a standard Agrobacterium-mediated root transformation protocol (Czako et al., Mol. Gen. Genet. 235, 33 (1992)). The presence of a transgene was determined by NPTII expression and resultant kanamycin resistance, and by DNA blot analysis. Several transgenic lines of the T3 generation homozygous for the sense or antisense transgenes were selected for further analyses.

Sugar sensitivity of transgenic plants was examined by performing bioassays using 6% glucose or 0.8 mM 2-deoxyglucose (2-dGlc), a nonmetabolizable glucose analog. On 6% glucose plates, greening and expansion of cotyledons, initiation of true leaves, and elongation of hypocotyl and root were suppressed in control (wild-type) Arabidopsis seedlings grown under constant light (FIG. 3A, right). These inhibitory effects caused by glucose were observed in six different Arabidopsis ecotypes including Bensheim (BE), C24, Columbia (Col), Landsberg erecta (Ler), RLD, and Wassilewskija (WS) (data not shown). In addition, the greening of cotyledons was found to be inhibited at a low concentration of 2-dGlc in control plants (FIG. 3B, right). This phenotype was consistent with the finding that 2-dGlc was capable of acting as a potent sugar signal that could trigger global repression of genes encoding photosynthetic proteins.

Compared to control plants, sense-AtHXK1 plants showed hypersensitivity to 6% glucose as indicated by stunted growth of the cotyledons, hypocotyl, and root (FIG. 3A, left). In contrast, anti-AtHXK1 plants turned green and elongated normally (FIG. 3A, middle), indicating that they were less sensitive to sugar. FIG. 3C illustrates that sugar hypersensitivity and insensitivity were displayed homogeneously in the T3 transgenic plant populations. As in the glucose assay, sense-AtHXK1 plants were hypersensitive to 2-dGlc as shown by the severe inhibition of greening of cotyledons (FIG. 3B, left; FIG. 3D, left). Anti-AtHXK1 plants were less sensitive to sugar and appeared green when germinated in the presence of 2-dGlc (FIG. 3B, middle; FIG. 3D, right).

As shown in Table 1 (below), similar phenotypes were observed in multiple independent transgenic lines generated with either sense or antisense AtHXK1 or AtHXK2. The scored phenotypes shown in Table 1 were determined based on the examination of light-grown, 7-day-old seedlings which were germinated on 1/2 MS plates containing either 6% glucose or 0.8 mM of 2-dGlc. Sugar insensitive (Ins), hypersensitive (Hyp), and ambiguous (A) phenotypes were scored and tabulated. The results of this analysis are presented in Table 1 (below).

TABLE 1

Sugar sensitivity in T3 homozygous transgenic plants.

| Transgenes | Total lines | 6% glucose | | | 0.8 mM 2-dGlc | | |
|---|---|---|---|---|---|---|---|
| | | Ins | Hyp | A | Ins | Hyp | A |
| CaMV35S:sense-AtHXK1 | 13 | 0 | 11 | 2 | 0 | 13 | 0 |
| CaMV35S:sense-AtHXK2 | 13 | 2* | 8 | 3 | 1* | 12 | 0 |
| CaMV35S:anti-AtHXK1 | 14 | 9 | 3 | 2 | 13 | 0 | 1 |
| CaMV35S:anti-AtHXK1 | 14 | 10 | 0 | 4 | 11 | 1 | 2 |

*Sugars insensitivity is believed to result from co-suppression.

To rule out the possibility that the difference in sugar sensing between transgenic and control plants was due to an osmotic effect, mannitol and 3-O-methylglucose (3-MeGlc) were used in control experiments. No apparent difference was observed between control and transgenic plants when plated on 6% mannitol (FIG. 3E) or 6% 3-MeGlc, a glucose analog which is not phosphorylated by HXK (FIG. 3F). Together, these results indicated that sugar sensing in transgenic plants was specific, because neither mannitol nor 3-MeGlc were able to replace glucose and interact with AtHXKs.

AtHXK Mediates Sugar Effects on Plant Growth and Development

We next compared the effects of sugar on hypocotyl and cotyledon development in both wild-type and transgenic plants. For these experiments, Arabidopsis seedlings were grown on plates containing 2–6% glucose for six days in the dark. Since hypocotyl elongation occurs more in the dark, the inhibitory effect caused by sugar could be visually evaluated. Because light triggers cotyledon expansion and greening, these dark-grown seedlings were exposed to light for 12 hours to determine the effect of sugar on cotyledon development. Our results are shown in FIG. 4.

In particular, in control plants, the hypocotyl length was inversely proportional to the glucose concentration (FIG. 4A). Under similar growth conditions, the sense-AtHXK plants were hypersensitive to sugar as revealed by the reduction of hypocotyl length when grown in the presence of 3–6% glucose (FIG. 4B). In contrast, anti-AtHXK plants were able to elongate even in the presence of 5 or 6% glucose (FIG. 4C). Although glucose concentrations below 2% promoted seedling growth in the presence of other nutrients (data not shown), hypocotyl inhibition by glucose concentrations above 2% reflected sugar-sensing mediated through AtHXK.

In contrast to light, glucose (at 4–6%) suppressed cotyledon greening and expansion in control plants (FIG. 4A). In sense-AtHXK plants, the impairment was greater as indicated by etiolated cotyledons (FIG. 4B). However, anti-AtHXK plants were found to be less sensitive to all glucose concentrations and turned green normally (FIG. 4C). Sugar inhibition of cotyledon development is explained by the plant's ability to switch to heterotrophic growth in the presence of abundant external sugars rather than photoautotrophic growth for which cotyledon expansion and greening are required. We also observed that there was a lack of sugar inhibition in dark-grown roots of control and antisense seedlings (FIG. 4A and FIG. 4C). This could be the consequence of low AtHXK expression in roots in the dark because ectopic AtHXK expression conferred glucose-dependent inhibition of root growth in sense plants (FIG. 4B). These results indicated that distinct sugar responses could occur in different tissues due to differential expression of AtHXK (FIG. 2).

AtHXK Mediates Sugar Repression and Activation of Gene Expression

To determine whether HXK was involved in sugar regulation of gene expression, we compared the expression levels of two sugar-repressible genes, the light-harvesting chlorophyll a/b binding protein (CAB1) and the ribulose bisphosphate carboxylase small subunit (RBCS), and one sugar-inducible gene, the nitrate reductase (NR1) gene in control, sense-, and anti-AtHXK plants (Sheen, Photosynthesis Res. 39, 427 (1994); Thomas and Rodriguez, Plant Physiol. 106, 1235 (1994); Cheng et al., Proc. Natl. Acad. Sci. U.S.A. 89, 1861 (1992)).

We first examined illuminated dark-grown etiolated seedlings propagated on 6% glucose as described above. RNA blot analyses were performed using 1.1 kb CAB1, 0.5 kb RBCS, and 3.2 kb NR1 probes from Arabidopsis; also as described above.

The transcription levels of CAB1 and RBCS were low in control plants, and nearly abolished in both sense-AtHXK1 and sense-AtHXK2 plants exhibiting sugar hypersensitivity (FIG. 5A). In contrast, both genes were expressed at high levels in both anti-AtHXK plants indicating sugar insensitivity. Consistent with the notion that sense transgenic plants are hypersensitive to sugars, NR1 was activated in both sense-AtHXK1 and sense-AtHXK2 plants, but not in anti-AtHXK or control plants (FIG. 5A). Together, these data indicated that AtHXK was the sensor which mediated both sugar-repressible and sugar-inducible gene expression in higher plants. In addition, the transcription levels of CAB1 and RBCS were similar in sense-AtHXKs and control plants grown in the absence of sugars (data not shown), indicating that sugar sensing by the AtHXKs was specific, and that exogenous sugar was at least one signal used in illuminated etiolated seedlings.

To show that AtHXK regulated gene expression under physiological conditions, we examined CAB1 and RBCS expression in light-grown green plants without the addition of exogenous sugars (as described above). The results from these experiments showed that the transcript levels of both genes were nearly five-fold lower in sense-AtHXK plants than in anti-AtHXK or control plants (FIG. 5B). This differential expression was perhaps due to the repression of light inducibility by endogenous sugars mediated through the increased expression of AtHXK, because both genes showed uniformly low expression in the dark in transgenic and control plants (FIG. 5B) (data not shown for AtHXK2).

Altered AtHXK Expression in Transgenic Plants

To confirm that the observed sugar hypersensitivity or insensitivity in transgenic plants correlated with transgene expression, RNA and protein blot analyses were conducted as follows. RNA blot analyses were performed using gene- and strand-specific probes for the sense and antisense constructs which were expressed in the transgenic plants. Probes were synthesized using a polymerase chain reaction (PCR) method described by Greenberg et al. (*Cell* 77, 551 (1994)). Oligonucleotides for use as PCR primers were designed from the sequence of AtHXK1 (SEQ ID NO: 3) and AtHXK2 (SEQ ID NO: 4), and were used to amplify their respective cDNA fragments. The sense primers were 5'-ATGGGTAAAGTAGCTGTT-3' (SEQ ID NO: 10) and 5'-ATGGGTAAAGTGGCAGTTGCAA-3' (SEQ ID NO: 11) for AtHXK1 and AtHXK2, respectively. The antisense primers were 5'-TTAAGAGTCTTCAAGGTAGAG-3' (SEQ ID NO: 12) and 5'-TTAACTTGTTTCAGAGTCATCTTC-3' (SEQ ID NO: 13) for AtHXK1 and AtHXK2, respectively. Plasmids (pBluescript™ KS+) containing either AtHXK1 or AtHXK2 full-length cDNAs were used as templates for the PCR reactions. RNAs were extracted from illuminated etiolated seedlings grown on 6% glucose plates, gel fractionated, blotted to nylon membranes, and hybridized with each probe as described above. In illuminated etiolated seedlings, the transcript levels of AtHXK1 (sense-1) in sense-AtHXK1 plants and AtHXK2 (sense-2) in sense-AtHXK2 plants were more than 20-fold higher than control plants (FIG. 5C). In antisense plants, antisense RNAs of AtHXK1 (anti-1) and AtHXK2 (anti-2) were expressed in their respective antisense transgenic plants. In contrast, the endogenous transcript of AtHXK1 in anti-AtHXK1 and anti-AtHXK2 plants was reduced to less than 20% of the control level (FIG. 5C).

Longer exposure of the sense-2 blot revealed that the endogenous AtHXK2 expression in anti-AtHXK1 and anti-AtHXK2 plants was also reduced (data not shown). These results indicated that either antisense AtHXK1 or antisense AtHXK2 RNA was capable of reducing the endogenous RNA levels of both AtHXK1 and AtHXK2, presumably because of the high level of sequence identity. Similar results were obtained when 15-day-old, light-grown green transgenic plants were analyzed (data not shown).

Protein blot analyses were also performed with seedlings which were germinated and grown in the dark for 6 days on plates containing 1/2 MS medium with or without 6% glucose, and then exposed to white light (120 AE $m^{-2}s^{-1}$) for 4 hours. These analyses were also performed using protein extracted from fifteen-day-old light-grown green plants which were dark adapted for 3 days and then illuminated for 4 hours. Antibodies which were used in these experiments were prepared as follows. AtHXK1 containing the entire open reading frame was subcloned into the plasmid vector pET-19b (Novagen) for overexpression in Escherichia coli according to standard methods. Overexpressed AtHXK1 was then gel purified and used for the production of rabbit polyclonal antibodies. The antibodies were affinity purified, and protein blot analyses were performed using the Phototope™-Star Western Blot Detection Kit (New England Biolabs). Protein was extracted according to conventional methods (Wei et al., *Cell* 78, 1994; Tots et al. *EMBO J.* 6, 1843 (1987)).

The results of the protein blot experiments showed that AtHXK1 expression was 5 to 10 fold higher in sense-AtHXK1 than in control plants. In anti-AtHXK1 plants, the level of AtHXK1 was significantly lower than in control plants, although it was not completely eliminated (FIG. 5D).

Hexose Phosphorylation Activities in Transgenic Plants

To determine whether the altered AtHXK expression affected the total catalytic activities of hexose phosphorylation in transgenic plants, we performed a series of standard hexose phosphorylation assays as described by Renz and Stitt (*Planta* 190, 166 (1993)).

In illuminated etiolated seedlings (grown as described above), sense-AtHXK1 plants were found to possess the highest hexose phosphorylation activity, whereas other plants displayed lower activities (FIG. 5E). The higher activity detected in plants having increased expression of the AtHXK gene was consistent with the result of a yeast transformation experiment indicating that AtHXK1 had higher catalytic activity than AtHXK2 (data not shown).

We also carried out the enzymatic assay using fifteen-day-old, light-grown green plants that were dark-adapted for 3 days and illuminated for 4 hours. As shown in FIG. 5F, both sense-AtHXK1 and sense-AtHXK2 plants had higher hexose phosphorylation activities than anti-AtHXK and control plants. Together, these data provided evidence for the conclusion that the manipulation of AtHXK expression is sufficient to alter sugar-sensing and sugar-regulated activities in Arabidopsis. Therefore, the specific interaction between sugars and HXK, for example, AtHXK1 and AtHXK2, but not the total catalytic activity of HXK, was shown to be a key determinant of sugar-sensing mechanisms in plants.

Sugar Signaling is Uncoupled From Sugar Metabolism in Plants

The above observations suggested the existence of a regulatory function for HXK, and the uncoupling of sugar signaling from metabolism in plants. To confirm this hypothesis, we sought to increase the expression of a heterologous HXK that would provide excess catalytic activity for sugar metabolism, but no regulatory function. The yeast HXK2 (YHXK2) has been proposed to have catalytic and regulatory functions, and appeared to be a good candidate for this experiment (Entian, *Mol. Gen. Genet.* 178, 633 (1980); Entian and Frshlich, *J. Bacteriol.* 158, 29 (1984); Entian et al., *Mol. Cell. Biol.* 5, 3035 (1985)). We first determined whether the putative regulatory functions of the YHXK2 and AtHXK were interchangeable by examining the effect of increasing the expression of AtHXK on glucose repression in a yeast hxk1/hxk2 double mutant (DBY2219). The assay was based on the YHXK2-mediated growth inhibition (i.e., glucose repression) of wild-type yeast cells on a 2-dGlc/raffinose plate. The glucose repression assay was performed using a YP plate with 2% raffinose as the carbon source in the presence of 2-deoxyglucose (0.02%) as described by Ma et al. (*Mol. Cell. Biol.* 9, 5643 (1989)). The glucose analog, 2-dGlc, mimics glucose by inducing strong repression of the invertase gene (SUC2), but is itself unavailable for use as a carbon source. Thus, wild-type yeast strains exhibit glucose repression and cannot grow under these assay conditions; in contrast, in the hxk1/hxk2 double mutant, SUC2 expression is derepressed, allowing raffinose hydrolysis and the release of fructose for growth on assay plates. As shown in FIG. 6A, DBY2219 grew on a 2-dGlc/raffinose plate due to the lack of YHXK2 and derepression of invertase gene expression. However, growth of this strain was inhibited upon transformation with YHXK2 and restoration of glucose repression (FIG. 6A) (Ma and Botstein, *Mol. Cell. Biol.* 6, 4046 (1986); Ma et al., *Mol. Cell. Biol.* 9, 5643 (1989)).

To determine the effect of increasing the expression of YHXK2 in plants, a transgene construct, pCaMV35S-YHXK2, that expressed YHXK2 was introduced into Arabidopsis using the Agrobacterium-mediated protocol described above. Transgenic plants having increased expression of YHXK2 (YHXK2 plants) were observed to display sugar insensitivity in many assays. For instance, YHXK2 seedlings were less sensitive to 6% glucose than control and sense-AtHXK plants. Hypocotyl elongation, root growth, and greening of cotyledons were found to be inhibited in sense-AtHXK1 or control plants, but not in YHXK2 plants (FIG. 6B). RNA blot analysis showed that CAB1 and RBCS transcripts were not repressed in YHXK2 plants, whether grown with or without exogenous glucose (data not shown).

To insure that YHXK2 provided hexose phosphorylation activity in plants, enzymatic assays were conducted using both etiolated and green transgenic plants. FIG. 6C shows that total hexose phosphorylation activity was much higher in YHXK2 than in control plants, and similar to or higher than sense-AtHXK plants. However, YHXK2 plants were sugar-insensitive rather than hypersensitive (FIG. 6B). This dominant interfering effect of YHXK2 in transgenic plants presumably resulted from the increased expression of YHXK2 which competed with AtHXK for sugars, but which was incapable of transmitting a signal. We ruled out the possibility of gene silencing effects based on the normal expression of AtHXK1 and ATHXK2 in YHXK2 plants (data not shown).

These experiments indicated that the catalytic function of HXK was interchangeable between yeast and plants, but not the regulatory function for sugar-signaling. Our recent results have also shown that a third AtHXK does not complement HXK regulatory function (data not shown). Thus, glucose-signaling does not require extensive metabolism and is diminished when YHXK2 is overexpressed in plants.

In sum, we have found that HXK mediates sugar-sensing in higher plants based on the analyses of transgenic plants with gain or loss of AtHXK function, and a dominant interfering YHXK2.

Isolation of Other HXK cDNAs and Genomic DNAs

Based on the isolation described herein of the aforementioned HXK genes and polypeptides, the isolation of additional plant HXK coding sequences is made possible using standard strategies and techniques that are well known in the art. For example, using all or a portion of the amino acid sequence of an HXK polypeptide, one may readily design HXK-specific oligonucleotide probes, including HXK degenerate oligonucleotide probes (i.e., a mixture of all possible coding sequences for a given amino acid sequence). These oligonucleotides may be based upon the sequence of either DNA strand and any appropriate portion of the HXK sequence (for example, FIGS. 1F–G; SEQ ID NOS: 3 and 4, respectively). General methods for designing and preparing such probes are provided, for example, in Ausubel et al., 1996, *Current Protocols in Molecular Biology*, Wiley Interscience, New York, and Berger and Kimmel, *Guide to Molecular Cloning Techniques*, 1987, Academic Press, New York. These oligonucleotides are useful for HXK gene isolation, either through their use as probes capable of hybridizing to HXK complementary sequences or as primers for various amplification techniques, for example, polymerase chain reaction (PCR) cloning strategies.

Hybridization techniques and screening procedures are well known to those skilled in the art and are described, for example, in Ausubel et al. (supra); Berger and Kimmel (supra); and Sambrook et al., *Molecular Cloning: A Laboratory Manual*, Cold Spring Harbor Laboratory Press, New York. If desired, a combination of different oligonucleotide probes may be used for the screening of a recombinant DNA library. The oligonucleotides may be detectably-labeled using methods known in the art and used to probe filter replicas from a recombinant DNA library. Recombinant DNA libraries are prepared according to methods well known in the art, for example, as described in Ausubel et al. (supra), or they may be obtained from commercial sources.

For detection or isolation of closely related HXK sequences having greater than 80% identity, high stringency conditions are preferably used; such conditions include hybridization at about 65° C. and about 50% formamide, a first wash at about 65° C., about 2×SSC, and 1% SDS, followed by a second wash at about 65° C. and about 0.1% SDS, and 1×SSC. Lower stringency conditions for detecting HXK genes having about 30–50% sequence identity to the HXK genes described herein include, for example, hybridization at about 45° C. in the absence of formamide, a first wash at about 45° C., about 6×SSC, and about 1% SDS, and a second wash at about 50° C., about 6×SSC, and about 1% SDS. These stringency conditions are exemplary; other appropriate conditions may be determined by those skilled in the art.

As discussed above, HXK oligonucleotides may also be used as primers in amplification cloning strategies, for example, using PCR. PCR methods are well known in the art and are described, for example, in *PCR Technology, Erlich*, ed., Stockton Press, London, 1989*; PCR Protocols: A Guide to Methods and Applications*, Innis et al., eds., Academic Press, Inc., New York, 1990; and Ausubel et al. (supra). Primers are optionally designed to allow cloning of the amplified product into a suitable vector, for example, by including appropriate restriction sites at the 5' and 3' ends of the amplified fragment (as described herein). If desired, HXK may be isolated using the PCR "RACE" technique, or Rapid Amplification of cDNA Ends (see, e.g., Innis et al. (supra)). By this method, oligonucleotide primers based on an HXK sequence are oriented in the 3' and 5' directions and are used to generate overlapping PCR fragments. These overlapping 3'- and 5'-end RACE products are combined to produce an intact full-length cDNA. This method is described in Innis et al. (supra); and Frohman et al., *Proc. Natl. Acad. Sci. USA* 85, 8998, (1988).

Alternatively, any plant cDNA expression library may be screened by functional complementation of a yeast hxk1/hxk2 double mutant as described herein by Ma and Botstein, *Mol. Cell. Biol.* 6, 4046 (1986)).

Useful HXK sequences may be isolated from any appropriate organism. Confirmation of a sequence's relatedness to the HXK polypeptide family may be accomplished by a variety of conventional methods including, but not limited to, functional complementation assays and sequence comparison. In addition, the activity of any HXK sequence may be evaluated according to any of the techniques described herein.

Polypeptide Expression

HXK polypeptides may be produced by transformation of a suitable host cell with all or part of an HXK cDNA (for example, the cDNA described above) in a suitable expression vehicle or with a plasmid construct engineered for increasing the expression of an HXK polypeptide (supra) in vivo.

Those skilled in the field of molecular biology will understand that any of a wide variety of expression systems may be used to provide the recombinant protein. The precise host cell used is not critical to the invention. The HXK protein may be produced in a prokaryotic host, for example, *E. coli*, or in a eukaryotic host, for example, *Saccharomyces cerevisiae*, mammalian cells (for example, COS 1 or NIH 3T3 cells), or any of a number of plant cells including, without limitation, algae, tree species, ornamental species, temperate fruit species, tropical fruit species, vegetable species, legume species, monocots, dicots, or in any plant of commercial or agricultural significance. Particular examples of suitable plant hosts include, but are not limited to, Conifers, Petunia, Tomato, Potato, Tobacco, Arabidopsis, Lettuce, Sunflower, Oilseed rape, Flax, Cotton, Sugarbeet, Celery, Soybean, Alfalfa, Medicago, Lotus, Vigna, Cucumber, Carrot, Eggplant, Cauliflower, Horseradish, Morning Glory, Poplar, Walnut, Apple, Asparagus, Rice, Maize, Millet, Onion, Barley, Orchard grass, Oat, Rye, and Wheat.

Such cells are available from a wide range of sources including: the American Type Culture Collection (Rockland, Md.); or from any of a number seed companies, for example, W. Atlee Burpee Seed Co. (Warminster, Pa.), Park Seed Co. (Greenwood, S.C.), Johnny Seed Co. (Albion, Me.), or Northrup King Seeds (Harstville, S.C.). Descriptions and sources of useful host cells are also found in Vasil I.K., *Cell Culture and Somatic Cell Genetics of Plants*, Vol I, II, III Laboratory Procedures and Their Applications Academic Press, New York, 1984; Dixon, R. A., *Plant Cell Culture-A Practical Approach*, IRL Press, Oxford University, 1985; Green et al., *Plant Tissue and Cell Culture*, Academic Press, New York, 1987; and Gasser and Fraley, *Science* 244, 1293, (1989).

For prokaryotic expression, DNA encoding an HXK polypeptide is carried on a vector operably linked to control signals capable of effecting expression in the prokaryotic host. If desired, the coding sequence may contain, at its 5' end, a sequence encoding any of the known signal sequences capable of effecting secretion of the expressed protein into the periplasmic space of the host cell, thereby facilitating recovery of the protein and subsequent purification. Prokaryotes most frequently used are various strains of *E. coli*; however, other microbial strains may also be used. Plasmid vectors are used which contain replication origins, selectable markers, and control sequences derived from a species compatible with the microbial host. Examples of such vectors are found in Pouwels et al. (supra) or Ausubel et al. (supra). Commonly used prokaryotic control sequences (also referred to as "regulatory elements") are defined herein to include promoters for transcription initiation, optionally with an operator, along with ribosome binding site sequences. Promoters commonly used to direct protein expression include the beta-lactamase (penicillinase), the lactose (lac) (Chang et al., *Nature* 198, 1056 (1977)), the tryptophan (Trp) (Goeddel et al., *Nucl. Acids Res.* 8, 4057 (1980)), and the tac promoter systems, as well as the lambda-derived $P_L$ promoter and N-gene ribosome binding site (Simatake et al., *Nature* 292, 128 (1981)).

One particular bacterial expression system for HXK polypeptide production is the *E. coli* pET expression system (Novagen, Inc., Madison, Wis.). According to this expression system, DNA encoding an HXK polypeptide is inserted into a pET vector in an orientation designed to allow expression. Since the HXK gene is under the control of the T7 regulatory signals, expression of HXK is induced by inducing the expression of T7 RNA polymerase in the host cell. This is typically achieved using host strains which express T7 RNA polymerase in response to IPTG induction. Once produced, recombinant HXK polypeptide is then isolated according to standard methods known in the art, for example, those described herein.

Another bacterial expression system for HXK polypeptide production is the PGEX expression system (Pharmacia). This system employs a GST gene fusion system which is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

For eukaryotic expression, the method of transformation or transfection and the choice of vehicle for expression of the HXK polypeptide will depend on the host system selected. Transformation and transfection methods are described, e.g., in Ausubel et al. (supra); Weissbach and Weissbach, *Methods for Plant Molecular Biology*, Academic Press, 1989; Gelvin et al., *Plant Molecular Biology Manual*, Kluwer Academic Publishers, 1990; Kindle, K., *Proc. Natl. Acad. Sci., U.S.A* 87, 1228 (1990); Potrykus, I., *Annu. Rev. Plant Physiol. Plant Mol. Biology* 42, 205 (1991); and BioRad (Hercules, Calif.) Technical Bulletin #1687 (Biolistic Particle Delivery Systems). Expression vehicles may be chosen from those provided, e.g., in *Cloning Vectors: A Laboratory Manual* (P. H. Pouwels et al., 1985, Supp. 1987); Gasser and Fraley (supra); Clontech Molecular Biology Catalog (Catalog 1992/93 Tools for the Molecular Biologist, Palo Alto, Calif.); and the references cited above.

One preferred eukaryotic expression system is the mouse 3T3 fibroblast host cell transfected with a pMAMneo expression vector (Clontech). pMAMneo provides: an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding an HXK polypeptide is inserted into the pMAMneo vector in an orientation designed to allow expression. The recombinant HXK protein is then isolated as described below. Other preferable host cells which may be used in conjunction with the pMAMneo expression vehicle include COS cells and CHO cells (ATCC Accession Nos. CRL 1650 and CCL 61, respectively).

Alternatively, if desired, an HXK polypeptide is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the HXK polypeptide is cloned into an expression vector which includes the dihydrofolate reductase (DHFR) gene. Integration of the plasmid and, therefore, the HXK-encoding gene into the host cell chromosome is selected for by inclusion of 0.01–300 $\mu$M methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHrF and pAdD26SV(A) (described in Ausubel et al., supra). Any of the host cells described above or, preferably, a DHFR-deficient CHO cell line (for example, CHO DHFR$^-$cells, ATCC Accession No. CRL 9096) are among the host cells preferred for DHFR selection of a stably-transfected cell line or DHFR-mediated gene amplification.

Most preferably, an HXK polypeptide is produced by a stably-transfected plant cell line or by a transgenic plant. A number of vectors suitable for stable transfection of plant cells or for the establishment of transgenic plants are available to the public; such vectors are described in Pouwels et al. (supra), Weissbach and Weissbach (supra), and Gelvin et al. (supra). Methods for constructing such cell lines are described in, e.g., Weissbach and Weissbach (supra), and Gelvin et al. (supra). Typically, plant expression vectors include (1) a cloned plant gene under the transcriptional control of 5' and 3' regulatory sequences and (2) a dominant selectable marker. Such plant expression vectors may also contain, if desired, a promoter regulatory region (for example, one conferring inducible or constitutive, environmentally- or developmentally-regulated, or cell- or tissue-specific expression), a transcription initiation start site, a ribosome binding site, an RNA processing signal, a transcription termination site, and/or a polyadenylation signal.

Alternatively, the HXK polypeptide may be produced using a transient expression system (e.g., the maize transient expression system described by Sheen Plant Cell 2, 1027 (1990)).

Once the desired HXK nucleic acid sequences is obtained it may be manipulated in a variety of ways known in the art. For example, where the sequence involves non-coding flanking regions, the flanking regions may be subjected to mutagenesis.

The HXK DNA sequence of the invention may, if desired, be combined with other DNA sequences in a variety of ways. The HXK DNA sequence of the invention may be employed with all or part of the gene sequences normally associated with the HXK protein. In its component parts, a DNA sequence encoding an HXK protein is combined in a DNA construct having a transcription initiation control region capable of promoting transcription and translation in a host cell.

In general, the constructs will involve regulatory regions functional in plants which provide for modified production of HXK protein as discussed herein. The open reading frame coding for the HXK protein or functional fragment thereof will be joined at its 5' end to a transcription initiation regulatory region such as the sequence naturally found in the 5' upstream region of the HXK structural gene. Numerous other transcription initiation regions are available which provide for constitutive or inducible regulation.

For applications when developmental, cell, tissue, hormonal, or environmental expression is desired, appropriate 5' upstream non-coding regions are obtained from other genes; for example, from genes regulated during seed development, embryo development, or leaf development.

Regulatory transcript termination regions may also be provided in DNA constructs of this invention as well. Transcript termination regions may be provided by the DNA sequence encoding the HXK protein or any convenient transcription termination region derived from a different gene source. The transcript termination region will contain preferably at least 1–3 kb of sequence 3' to the structural gene from which the termination region is derived. Plant expression constructs having HXK as the DNA sequence of interest for expression (in either the sense or antisense orientation) thereof may be employed with a wide variety of plant life, particularly plant life involved in the production of storage reserves (for example, those involving carbon and nitrogen metabolism). Such genetically-engineered plants are useful for a variety of industrial and agricultural applications as discussed below. Importantly, this invention is applicable to dicotyledons and monocotyledons, and will be readily applicable to any new or improved transformation or regeneration method.

An example of a useful plant promoter according to the invention is a caulimovirus promoter, for example, a cauliflower mosaic virus (CaMV) promoter. These promoters confer high levels of expression in most plant tissues, and the activity of these promoters is not dependent on virally encoded proteins. CaMV is a source for both the 35S and 19S promoters. In most tissues of transgenic plants, the CaMV 35S promoter is a strong promoter (see, e.g., Odell et al., *Nature* 313, 810 (1985)). The CaMV promoter is also highly active in monocots (see, e.g., Dekeyser et al., Plant Cell 2, 591 (1990); Terada and Shimamoto, *Mol. Gen. Genet.* 220, 389, (1990)). Moreover, activity of this promoter can be further increased (i.e., between 2–10 fold) by duplication of the CaMV 35S promoter (see e.g., Kay et al., *Science* 236, 1299 (1987); Ow et al., *Proc. Natl. Acad. Sci., U.S.A.* 84, 4870 (1987); and Fang et al., *Plant Cell* 1, 141 (1989)).

Other useful plant promoters include, without limitation, the nopaline synthase promoter (An et al., *Plant Physiol.* 88, 547 (1988)) and the octopine synthase promoter (Fromm et al., *Plant Cell* 1, 977 (1989)).

For certain applications, it may be desirable to produce the HXK gene product in an appropriate tissue, at an appropriate level, or at an appropriate developmental time. For this purpose, there are an assortment of gene promoters, each with its own distinct characteristics embodied in its regulatory sequences, shown to be regulated in response to the environment, hormones, and/or developmental cues. These include gene promoters that are responsible for heat-regulated gene expression (see, e.g., Callis et al., *Plant Physiol.* 88, 965 (1988); Takahashi and Komeda, *Mol. Gen. Genet.* 219, 365 (1989); and Takahashi et al. *Plant J.* 2, 751 (1992)), light-regulated gene expression (e.g., the pea rbcS-3A described by Kuhlemeier et al., *Plant Cell* 1, 471 (1989); the maize rbcS promoter described by Schäffner and Sheen, *Plant Cell* 3, 997 (1991); or the cholorphyll a/b-binding protein gene found in pea described by Simpson et al., *EMBO J.* 4, 2723 (1985)), hormone-regulated gene expression (for example, the abscisic acid (ABA) responsive sequences from the Em gene of wheat described by Marcotte et al., *Plant Cell* 1, 969 (1989); the ABA-inducible HVA1 and HVA22, and rd29A promoters described for barley and Arabidopsis by Straub et al., *Plant Cell* 6, 617 (1994), Shen et al., *Plant Cell* 7, 295 (1994), and Yamaguchi-Shinosaki et al wound-induced gene expression (for example, of wunI described by Siebertz et al., *Plant Cell* 1, 961 (1989)), or organ-specific gene expression (for example, of the tuber-specific storage protein gene described by Roshal et al., *EMBO J.* 6, 1155 (1987); the 23-kDa zein gene from maize described by Schernthaner et al., *EMBO J.* 7, 1249 (1988); or the French bean β-phaseolin gene described by Bustos et al., *Plant Cell* 1, 839 (1989)).

Plant expression vectors may also optionally include RNA processing signals, e.g, introns, which have been shown to be important for efficient RNA synthesis and accumulation (Callis et al., *Genes and Dev.* 1, 1183 (1987)). The location of the RNA splice sequences can dramatically influence the level of transgene expression in plants. In view of this fact, an intron may be positioned upstream or downstream of an HXK polypeptide-encoding sequence in the transgene to modulate levels of gene expression.

In addition to the aforementioned 5' regulatory control sequences, the expression vectors may also include regulatory control regions which are generally present in the 3' regions of plant genes (Thornburg et al., *Proc. Natl. Acad. Sci. U.S.A.* 84, 744 (1987); An et al., *Plant Cell* 1, 115 (1989)). For example, the 3' terminator region may be included in the expression vector to increase stability of the mRNA. One such terminator region may be derived from the PI-II terminator region of potato. In addition, other commonly used terminators are derived from the octopine or nopaline synthase signals.

The plant expression vector also typically contains a dominant selectable marker gene used to identify those cells that have become transformed. Useful selectable genes for plant systems include genes encoding antibiotic resistance genes, for example, those encoding resistance to hygromycin, kanamycin, bleomycin, G418, streptomycin or spectinomycin. Genes required for photosynthesis may also be used as selectable markers in photosynthetic-deficient strains. Alternatively, the green-fluorescent protein from the jellyfish *Aequorea victoria* may be used as a selectable marker (Sheen et al., *Plant J.* 8:777, 1995; Chiu et al., *Current Biology* 6, 325 (1996)). Finally, genes encoding herbicide resistance may be used as selectable markers; useful herbicide resistance genes include the bar gene encoding the enzyme phosphinothricin acetyltransferase and conferring resistance to the broad spectrum herbicide Basta® (Hoechst AG, Frankfurt, Germany).

Efficient use of selectable markers is facilitated by a determination of the susceptibility of a plant cell to a particular selectable agent and a determination of the concentration of this agent which effectively kills most, if not all, of the transformed cells. Some useful concentrations of antibiotics for tobacco transformation include, e.g., 75–100 μg/ml (kanamycin), 20–50 μg/ml (hygromycin), or 5–10 μg/ml (bleomycin). A useful strategy for selection of transformants for herbicide resistance is described, e.g., by Vasil et al., supra.

It should be readily apparent to one skilled in the art of molecular biology, especially in the field of plant molecular biology, that the level of gene expression is dependent, not only on the combination of promoters, RNA processing signals, and terminator elements, but also on how these elements are used to increase the levels of selectable marker gene expression.

Plant Transformation

Upon construction of the plant expression vector, several standard methods are available for introduction of the vector into a plant host, thereby generation a transgenic plant. These methods include (1) Agrobacterium-mediated transformation (*A. tumefaciens* or *A. rhizogenes*) (see, e.g., Lichtenstein and Fuller In: *Genetic Engineering*, vol 6, PWJ Rigby, ed, London, Academic Press, 1987; and Lichtenstein, C. P., and Draper, J,. In: *DNA Cloning*, Vol II, D. M. Glover, ed, Oxford, IRI Press, 1985)), (2) the particle delivery system (see, e.g., Gordon-Kamm et al., *Plant Cell* 2, 603 (1990); or BioRad Technical Bulletin 1687, supra), (3) microinjection protocols (see, e.g., Green et al., supra), (4) polyethylene glycol (PEG) procedures (see, e.g., Draper et al., *Plant Cell Physiol.* 23, 451 (1982); or e.g., Zhang and Wu, *Theor. Appl. Genet.* 76, 835 (1988)), (5) liposome-mediated DNA uptake (see, e.g., Freeman et al., *Plant Cell Physiol.* 25, 1353 (1984)), (6) electroporation protocols (see, e.g., Gelvin et al., supra; Dekeyser et al., supra; Fromm et al., *Nature* 319, 791 (1986); Sheen *Plant Cell* 2, 1027 (1990); or Jang and Sheen *Plant Cell* 6, 1665 (1994)), and (7) the vortexing method (see, e.g., Kindle supra). The method of transformation is not critical to the instant invention. Any method which provides for efficient transformation may be employed. As newer methods are available to transform crops or other host cells, they may be directly applied.

The following is an example out-lining one particular technique, an Agrobacterium-mediated plant transformation. By this technique, the general process for manipulating genes to be transferred into the genome of plant cells is carried out in two phases. First, cloning and DNA modification steps are carried out in *E. coli*, and the plasmid containing the gene construct of interest is transferred by conjugation or electroporation into Agrobacterium. Second, the resulting Agrobacterium strain is used to transform plant cells. Thus, for the generalized plant expression vector, the plasmid contains an origin of replication that allows it to replicate in Agrobacterium and a high copy number origin of replication functional in *E. coli*. This permits facile production and testing of transgenes in *E. coli* prior to transfer to Agrobacterium for subsequent introduction into plants. Resistance genes can be carried on the vector, one for selection in bacteria, for example, streptomycin, and another that will function in plants, for example, a gene encoding kanamycin resistance or herbicide resistance. Also present on the vector are restriction endonuclease sites for the addition of one or more transgenes and directional T-DNA border sequences which, when recognized by the transfer functions of Agrobacterium, delimit the DNA region that will be transferred to the plant.

In another example, plant cells may be transformed by shooting into the cell tungsten microprojectiles on which cloned DNA is precipitated. In the Biolistic Apparatus (Bio-Rad) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to pass through. As a result, the plastic macroprojectile smashes against the stopping plate, and the tungsten microprojectiles continue toward their target through the hole in the plate. For the instant invention the target can be any plant cell, tissue, seed, or embryo. The DNA introduced into the cell on the microprojectiles becomes integrated into either the nucleus or the chloroplast.

In general, transfer and expression of transgenes in plant cells are now routine practices to those skilled in the art, and have become major tools to carry out gene expression studies in plants and to produce improved plant varieties of agricultural or commercial interest.

Transgenic Plant Regeneration

Plants cells transformed with a plant expression vector can be regenerated, for example, from single cells, callus tissue, or leaf discs according to standard plant tissue culture techniques. It is well known in the art that various cells, tissues, and organs from almost any plant can be successfully cultured to regenerate an entire plant; such techniques are described, e.g., in Vasil supra; Green et al., supra; Weissbach and Weissbach, supra; and Gelvin et al., supra.

In one particular example, a cloned HXK polypeptide or an antisense construct under the control of the 35S CaMV promoter and the nopaline synthase terminator and carrying a selectable marker (for example, kanamycin resistance) is transformed into Agrobacterium. Transformation of leaf discs (for example, of tobacco leaf discs), with vector-containing Agrobacterium is carried out as described by Horsch et al. (*Science* 227, 1229 (1985)). Putative transformants are selected after a few weeks (for example, 3 to 5 weeks) on plant tissue culture media containing kanamycin (e.g. 100 μg/ml). Kanamycin-resistant shoots are then placed on plant tissue culture media without hormones for root initiation. Kanamycin-resistant plants are then elected for greenhouse growth. If desired, seeds from elf-fertilized transgenic plants can then be sowed in a oil-less medium and grown in a greenhouse. Kanamycin-esistant progeny are selected by sowing surfaced sterilized seeds on hormone-free kanamycin-containing media. Analysis for the integration of the transgene is accomplished by standard techniques (see, for example, Ausubel et al. supra; Gelvin et al. supra).

Transgenic plants expressing the selectable marker are then screened for transmission of the transgene DNA by standard immunoblot and DNA detection techniques. Each positive transgenic plant and its transgenic progeny are unique in comparison to other transgenic plants established with the same transgene. Integration of the transgene DNA into the plant genomic DNA is in most cases random, and the site of integration can profoundly effect the levels and the tissue and developmental patterns of transgene expression. Consequently, a number of transgenic lines are usually screened for each transgene to identify and select plants with the most appropriate expression profiles.

Transgenic lines are evaluated on levels of transgene expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, e.g., Ausubel et al., supra). The RNA-positive plants are then analyzed for protein expression by Western immunoblot analysis using HXK specific antibodies (see, e.g., Ausubel et al., supra). In addition, in situ hybridization and immunocytochemistry according to standard protocols can be done using transgene-specific nucleotide probes and antibodies, respectively, to localize sites of expression within transgenic tissue.

Once the recombinant HXK protein is expressed in any cell or in a transgenic plant (for example, as described above), it may be isolated, e.g., using affinity chromatography. In one example, an anti-HXK antibody (e.g., produced as described in Ausubel et al., supra, or by any standard technique) may be attached to a column and used to isolate the polypeptide. Lysis and fractionation of HXK-producing cells prior to affinity chromatography may be performed by standard methods (see, e.g., Ausubel et al., supra). Once isolated, the recombinant protein can, if desired, be further purified, for example, by high performance liquid chromatography (see, e.g., Fisher, *Laboratory Techniques In Biochemistry And Molecular Biology*, eds., Work and Burdon, Elsevier, 1980).

These general techniques of polypeptide expression and purification can also be used to produce and isolate useful HXK fragments or analogs.

Use

The invention described herein is useful for a variety of agricultural and commercial purposes including, but not limited to, increasing crop yields, improving crop and ornamental quality, and reducing agricultural production costs. For example, the methods, DNA constructs, proteins, and transgenic plants described herein are useful for improving fruit and vegetable characteristics including: taste, texture, size, color, acidity or sweetness; nutritional content; disease resistance; and ripening processes.

Our results presented above demonstrate that it is possible to modulate hexokinase gene expression in transgenic plants by providing for the transcription of a hexokinase sequence that is complementary to the mRNA of an endogenous plant hexokinase. In this manner, various plant processes can be modified, controlled, or manipulated, resulting in enhancement of production of carbohydrate (e.g., sucrose and starch) products, changes in plant growth, cellular differentiation and development, changes in plant phenotypes, and alteration of carbon/nitrogen partitioning and accumulation. In addition, as is discussed above, antisense expression can be controlled, if desired, in a cell-, tissue-, organ-, or developmentally-specific manner. Thus, the use of antisense control can provide for substantial inhibition or varying degrees of reduction of hexokinase gene expression. In this manner, cellular phenotypes can be modified without the production of extraneous proteins and with particular targeting to a specific gene.

For example, transgenic plants expressing antisense hexokinase RNA constructs are useful for eliminating feedback inhibition of photosynthesis (for example, by sugar induced repression of photosynthetic genes) that is caused by the accumulation of sugar metabolites (for example, the photosynthetic endproducts sucrose and glucose). As shown herein, transgenic plants expressing antisense hexokinase genes are less sensitive to sugar, and are no longer subject to growth limitations and restrictions that are the result of sugar repression (for example, reduction of photosynthetic gene expression). In particular, we have discovered that transgenic plants expressing antisense hexokinase genes develop normally and thrive under conditions that typically limit and restrict plant growth due to feedback inhibition (for example, in wild-type plants shoot development is blocked by high hexose concentrations, but transgenic plants expressing antisense hexokinase shoot development proceeds normally). Thus transgenic plants expressing antisense hexokinase are useful for a variety of agricultural purposes including, but not limited to, the promotion of growth rate and development, seed germination, the stimulation of flowering, and improvement of crop yield, especially under adverse environmental conditions, for example, high light, high temperature, and high $CO_2$.

In addition, the results presented above demonstrate that it is possible to modulate a plant's sensitivity to sugar by increasing levels of hexokinase protein. In particular, we found that increased levels of hexoki-nase protein are useful for promoting increased expression of a sugar-activated gene (for example, NR1). In this manner, various plant processes that are controlled, modulated, or activated by sugar can be regulated or manipulated by increasing the levels of hexokinase protein in a given plant cell, tissue, or organ. Such genetic engineering of gene expression is useful for enhancing storage protein accumulation and nitrogen accumulation, improving plant wounding responses and pathogen defense mechanisms, as well as for modifying pigmentation (for example, anthocyanin) of plant tissues (for example, fruits and flowers) for ornamental and horticultural purposes. For example, increased expression of hexokinase is useful for manipulating or promoting the expression of a wide variety of sugar-activated genes that encode an assortment of proteins including, but not limited to, potato storage protein patatin, soybean vegetative storage protein, sporamin, proteinase inhibitor II, sucrose phosphate synthase, rice and maize sucrose synthase, chalcone synthase, and nitrate reductase.

All publications and patents mentioned in this specification are herein incorporated by reference to the same extend as if each individual publication or patent was specifically and individually indicated to be incorporated by reference.

Other Embodiments

From the foregoing description, it will be apparent that variations and modifications may be made to the invention described herein to adopt it to various usages and conditions. Such embodiments are also within the scope of the following claims.

What is claimed is:

1. A method for modifying sugar sensitivity in a transgenic plant cell by increasing the level of a hexokinase protein in said transgenic plant cell, said method comprising expressing in said transgenic plant cell a hexokinase nucleic acid sequence that specifically hybridizes under highly stringent conditions to the complement of the sequence set forth in SEQ ID NO.: 3 or SEQ ID NO.: 4, wherein said highly stringent conditions comprise
   a) hybridization at 65° C. and 50% formamide,
   b) a first wash at 65° C., 2×SSC, and 1% SDS, and
   c) a second wash at 65° C., 1×SSC, and 0.1% SDS;
   and said nucleic acid encodes a hexokinase protein comprising a sugar binding domain, wherein expression of said hexokinase nucleic acid sequence increases the level of said hexokinase protein in said transgenic plant cell.

2. The method of claim 1, wherein said hexokinase nucleic acid sequence comprises the AtHXK1 nucleotide sequence that is shown FIG. 1F (SEQ ID NO: 3).

3. The method of claim 1, wherein said hexokinase nucleic acid sequence comprises the AtHXK2 nucleotide sequence that is shown FIG. 1G (SEQ ID NO: 4).

4. The method according to claim 1, wherein said transgenic plant has an increased sensitivity to sugar.

5. The method of claim 1, wherein expression of said hexokinase nucleic acid sequence enhances a pathogen defense mechanism.

6. The method of claim 1, wherein expression of said hexokinase nucleic acid sequence enhances a wounding response.

7. The method of claim 1, wherein expression of said hexokinase nucleic acid sequence enhances starch or sucrose synthesis.

8. The method of claim 1, wherein expression of said hexokinase nucleic acid sequence enhances storage protein accumulation.

9. The method of claim 1, wherein expression of said hexokinase nucleic acid sequence enhances nitrogen accumulation.

10. The method of claim 1, wherein expression of said hexokinase nucleic acid sequence promotes the expression of a sugar-activated gene.

11. The method of claim 10, wherein said sugar-activated gene encodes a potato storage protein, a soybean vegetative storage protein, a proteinase inhibitor, a sucrose phosphate synthase, a sucrose synthase, a chalcone synthase, or a nitrate reductase.

12. The method of claim 1, wherein expression of said hexokinase nucleic acid sequence modifies plant tissue pigmentation.

13. The method of claim 1, further comprising regenerating a transgenic plant from said plant cell expressing said hexokinase nucleic acid sequence.

* * * * *

UNITED STATES PATENT AND TRADEMARK OFFICE
CERTIFICATE OF CORRECTION

PATENT NO. : 6,632,602 B1
DATED : October 14, 2003
INVENTOR(S) : Sheen et al.

It is certified that error appears in the above-identified patent and that said Letters Patent is hereby corrected as shown below:

Column 5,
Line 34, "glycine alanine" should be -- glycine, alanine --.

Column 9,
Line 54, "mil48" should be -- mil48 --.

Column 10,
Line 65, "Suaar" should be -- Sugar --.

Column 18,
Line 38, "PGEX expression system" should be -- pGEX expression system --.

Column 19,
Line 8, "promotor" should be -- promoter --.

Column 21,
Line 17, "cholorphyll" should be -- chlorophyll --.

Column 23,
Line 55, "Kanamycin-esistant" should be -- Kanamycin-resistant --.

Column 25,
Line 4, "endproducts" should be -- end products --; and
Line 26, "hexoki-nase" should be -- hexokinase --.

Column 51,
Lines 28, 29 and 30, replace "65° C." with -- 65° C --.

Signed and Sealed this

First Day of February, 2005

JON W. DUDAS
*Director of the United States Patent and Trademark Office*